(12) United States Patent
Laird et al.

(10) Patent No.: US 9,290,803 B2
(45) Date of Patent: Mar. 22, 2016

(54) DNA METHYLATION ANALYSIS BY DIGITAL BISULFITE GENOMIC SEQUENCING AND DIGITAL METHYLIGHT

(75) Inventors: Peter W. Laird, South Pasadena, CA (US); Binh N. Trinh, Alhambra, CA (US); Mihaela Campan, Los Angeles, CA (US); Daniel J. Weisenberger, Playa Del Rey, CA (US)

(73) Assignee: University of Southern California, Los Angeles, CA (US)

( * ) Notice: Subject to any disclaimer, the term of this patent is extended or adjusted under 35 U.S.C. 154(b) by 62 days.

(21) Appl. No.: 12/102,783

(22) Filed: Apr. 14, 2008

(65) Prior Publication Data

US 2008/0254474 A1     Oct. 16, 2008

Related U.S. Application Data

(60) Provisional application No. 60/911,495, filed on Apr. 12, 2007.

(51) Int. Cl.
     C12Q 1/68       (2006.01)
(52) U.S. Cl.
     CPC .................................. C12Q 1/6869 (2013.01)
(58) Field of Classification Search
     None
     See application file for complete search history.

(56) References Cited

U.S. PATENT DOCUMENTS

| | | |
|---|---|---|
| 5,210,015 A | 5/1993 | Gelfand |
| 5,736,333 A | 4/1998 | Livak |
| 5,786,146 A | 7/1998 | Herman |
| 5,804,375 A | 9/1998 | Gelfand |
| 5,866,336 A | 2/1999 | Nazarenko |
| 5,876,930 A | 3/1999 | Livak |
| 6,017,704 A | 1/2000 | Herman |
| 6,140,054 A | 10/2000 | Wittwer |
| 6,270,967 B1 | 8/2001 | Whitcombe |
| 6,331,393 B1 | 12/2001 | Laird |
| 6,472,156 B1 | 10/2002 | Wittwer |

FOREIGN PATENT DOCUMENTS

| | | |
|---|---|---|
| EP | 1185695 | 11/2000 |
| WO | WO 97/46705 | 12/1997 |
| WO | WO 00/70090 | 11/2000 |

OTHER PUBLICATIONS

Khandurina et al. Analytical Chemistry vol. 72:2995-3000. 2000.*
Eads et al. (Nucleic Acids Research, 2000).*
Vogelstein et al. (PNAS, 1999).*
Lau et al. (Cancer Research, 2006).*
Donavan et al. (Blood, 2000, vol. 95, p. 2651-2658).*
Simmonds et al. (Journal of Virology, 1990, 64(2):864-872).*
U.S. Appl. No. 60/911,495, filed Apr. 12, 2007, Laird.
Ahern, "Biochemical, Reagent Kits Offer Scientists Good Return on Investment," The Scientist, Jul. 24, 1995, p. 20, vol. 9, Issue 15 (3 pages).
Ahuja et al., "Association between CpG Island Methylation and Microsatellite Instability in Colorectal Cancer," Cancer Research, Aug. 15, 1997, pp. 3370-3374, vol. 57.
Bender et al., "Inhibition of DNA Methylation by 5-Aza-2'-deoxycytidine Suppresses the Growth of Human Tumor Cell Lines," Cancer Research, Jan. 1, 1998, pp. 95-101, vol. 58.
Bernard et al., "Homogenous Multiplex Genotyping of Hemochromatosis Mutations with Fluorescent Hybridization Probes," American Journal of Pathology, 1998, pp. 1055-1061, vol. 153.
Bird, "CpG-rich islands and the function of DNA methylation," Nature, May 15, 1986, pp. 209-213, vol. 321.
Bird, "The Essentials of DNA Methylation," Cell, Jul. 10, 1992, pp. 5-8, vol. 70.
Cedar, "DNA Methylation and Gene Activity," Cell, Apr. 8, 1988, pp. 3-4, vol. 53.
Cottrell et al., "Sensitive Detection of DNA Methylation," Annals of the New York Academy of Sciences, 2003, pp. 120-130, vol. 983.
Cunningham et al., "Hypermethylation of the hMLH1 Promoter in Colon Cancer with Microsatellite Instability," Cancer Research, Aug. 1, 1998, pp. 3455-3460, vol. 58.
Eads et al., "CpG Island Hypermethylation in Human Colorectal Tumors Is Not Associated with DNA Methyltransferase Overexpression," Cancer Research, 1999, pp. 2302-2306, vol. 59.
Eads et al., "MethyLight: a high-throughput assay to measure DNA methylation," Nucleic Acids Research, 2000, pp. e32 (i-viii), vol. 28.
Fatemi et al., "Footprinting of mammalian promoters: use of a CpG DNA methyltransferase revealing nucleosome positions at a single molecule level," Nucleic Acids Research, 2005, pp. e176 (9 pages), vol. 33.

(Continued)

Primary Examiner — Stephanie K Mummert
(74) Attorney, Agent, or Firm — Barry L. Davison; Davis Wright Tremaine LLP

(57) ABSTRACT

Provided are novel sensitive methylation assays referred to herein as Digital MethyLight, comprising stochastically distributing and compartmentalizing bisulfite-treated genomic DNA over multiple PCR reaction wells for detection of individually methylated DNA molecules in a large background of unmethylated DNA. Digital Bisulfite Genomic DNA Sequencing methods are also provided for high-resolution DNA methylation information without subcloning. Background signal and PCR contaminants are diluted, while the ratio of primer to methylated template DNA is kept high. Preferably, biological fluid (e.g., urine, blood-based (e.g., plasma and/or serum)) samples are analyzed for cancer diagnosis, prognosis and surveillance. Multiplexed PCR formats may be implemented to enhance when using small DNA amounts. Compositions and methods for diagnosis and/or prognosis of breast cancer, comprising the use of FOXE1, CLDN5 and/or RUNX3 gene markers are also provided (SEQ ID NOS: 17, 16 and 18, respectively for respective CpG island sequences), and in preferred embodiments plasma or serum samples are used.

17 Claims, 5 Drawing Sheets

(56) References Cited

OTHER PUBLICATIONS

Fink et al., "Real-time quantitative RT-PCR after laser-assisted cell picking," Nature Medicine, Nov. 1998, pp. 1329-1333, vol. 4, No. 11.
Frommer et al., "A genomic sequencing protocol that yields a positive display of 5-methylcytosine residues in individual DNA strands," The Proceedings of the National Academy of Sciences, 1992, pp. 1827-1831, vol. 89.
Gardiner-Garden et al., "CpG Islands in Vertebrate Genomes," Journal of Molecular Biology, 1987, pp. 261-282, vol. 196.
Gibbs, "DNA Amplification by the Polymerase Chain Reaction," Analytical Chemistry, Jul. 1, 1990, pp. 1202-1214, vol. 62, No. 13.
Gonzalgo et al., "Identification and Characterization of Differentially Methylated Regions of Genomic DNA by Methylation-sensitive Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Heid et al., "Real Time Quantitative PCR," Genome Research, 1996, pp. 988-994, vol. 6.
Herman et al., "Incidence and functional consequences of hMLH1 promoter hypermethylation in colorectal carcinoma," The Proceedings of the National Academy of Sciences, Jun. 1998, pp. 6870-6875, vol. 95.
Herman et al., "Methylation-specific PCR: A novel PCR assay for methylation status of CpG islands," The Proceedings of the National Academy of Sciences, 1996, pp. 9821-9826, vol. 93.
Hiltunen et al., "Hypermethylation of the APC (Adenomatous Polyposis Coli) Gene Promoter Region in Human Colorectal Carcinoma," International Journal of Cancer, 1997, pp. 644-648, vol. 70.
Holland et al., "Detection of specific polymerase chain reaction product by utilizing the 5'→3' exonuclease activity of Thermus aquaticus DNA polymerase," The Proceedings of the National Academy of Sciences, 1991, pp. 7276-7280, vol. 88.
Hsieh et al., "Meddling with methylation," Nature Cell Biology, 2003, pp. 502-504, vol. 5.
Ibrahim et al., "Real-Time Microchip PCR for Detecting Single-Base Differences in Viral and Human DNA," Analytical Chemistry, 1998, pp. 2013-2017, vol. 70.
Ionov et al., "Ubiquitous somatic mutations in simple repeated sequences reveal a new mechanism for colonic carcinogenesis," Nature, Jun. 10, 1993, pp. 558-561, vol. 363, No. 6429.
Issa et al., "Methylation of the oestrogen receptor. CpG island links ageing and neoplasia in human colon," Nature Genetics, Aug. 1994, pp. 536-540, vol. 7, No. 4.
Jones, "DNA Methylation Errors and Cancer," Cancer Research, Jun. 1, 1996, pp. 2463-2467, vol. 56.
Jones et al., "The Epigenomics of Cancer," Cell, 2007, pp. 683-692, vol. 128.
Kane et al., "Methylation of the hMLH1 Promoter Correlates with Lack of Expression of hMLH1 in Sporatic Colon Tumors and Mismatch Repair-defective Human Tumor Cell Lines," Cancer Research, Mar. 1, 1997, pp. 808-811, vol. 57.
Kawai et al., "Comparison of DNA Methylation Patterns among Mouse Cell Lines by Restriction Landmark Genomic Scanning," Molecular and Cellular Biology, Nov. 1994, pp. 7421-7427, vol. 14, No. 11.
Klimasauskas et al., "HhaI Methyltransferase Flips Its Target Base Out of the DNA Helix," Cell, Jan. 28, 1994, pp. 357-369, vol. 76, No. 2.
Kubota et al., "A new assay for the analysis of X-chromosome inactivation based on methylation-specific PCR," Human Genetics, 1999, pp. 49-55, vol. 104.
Kuppuswamy et al., "Single nucleotide primer extension to detect genetic diseases: Experimental application to hemophilia B (factor IX) and cystic fibrosis genes," The Proceedings of the National Academy of Sciences, Feb. 1991, pp. 1143-1147, vol. 88.
Laird, "Cancer epigentics," Human Molecular Genetics, 2005, pp. R65-R76, vol. 14.
Laird et al., "DNA methylation and cancer," Human Molecular Genetics, 1994, pp. 1487-1495, vol. 3.
Laird, "The Power and the Promise of DNA Methylation Markers," Nature Reviews. Cancer, 2003, pp. 253-266, vol. 3.
Lau et al., "RUNX3 Is Frequently Inactivated by Dual Mechanisms of Protein Mislocalization and promoter hypermethylation in Breast Cancer," Cancer Research, 2006, pp. 6512-6520, vol. 66.
Lee et al., "Allelic discrimination by nick-translation PCR with fluorogenic probes," Nucleic Acids Research, 1993, pp. 3761-3766, vol. 21.
Lengauer et al., "DNA methylation and genetic instability in colorectal cancer cells," The Proceedings of the National Academy of Sciences, Mar. 1997, pp. 2545-2550, vol. 94.
Li et al., "Targeted Mutation of the DNA Methyltransferase Gene Results in Embryonic Lethality," Cell, Jun. 12, 1992, pp. 915-926, vol. 69.
Livak, "Allelic discrimination using fluorogenic probes and the 5' nuclease assay," Genetic Analysis, 1999, pp. 143-149, vol. 14.
Livak et al., "Oligonucleotides with Fluorescent Dyes at Opposite Ends Provide a Quenched Probe System Useful for Detecting PCR Product and Nucleic Acid Hybridization," PCR Methods and Applications, 1995, pp. 357-362, vol. 4.
Lo et al., "Quantitative Analysis of Aberrant p16 Methylation Using Real-Time Quantitative Methylation-specific Polymerase Chain Reaction," Cancer Research, 1999, pp. 3899-3903, vol. 59.
Lofton-Day et al., "Clinical case-control study in plasma shows that the DNA methylation biomarker, Septin 9, detects 70% of Stage I-III colorectal cancer patients," American Association of Cancer Research Annual Meeting, Apr. 14-18, 2007, Los Angeles, California (abstract only) (2 pages).
Mullis et al., "Specific Enzymatic Amplification of DNA In Vitro: The Polymerase Chain Reaction," Cold Spring Harbor Symposia on Quantitative Biology, 1986, pp. 263-273, vol. 51, Part 1.
Nazarenko et al., "A closed tube format for amplification and detection of Dna based on energy transfer," Nucleic Acids Research, 1997, pp. 2516-2521, vol. 25.
Ottesen et al., "Microfluidic Digital PCR Enables Multigene Analysis of Individual Environmental Bacteria," Science, 2006, pp. 1464-1467, vol. 314.
Parsons et al., "Microsatellite Instability and Mutations of the Transforming Growth Factor β Type II Receptor Gene in Colorectal Cancer," Cancer Research, Dec. 1, 1995, pp. 5548-5550, vol. 55.
Rein et al., "Identifying 5-methylcytosine and related modifications in DNA genomes," Nucleic Acids Research, 1998, pp. 2255-2264, vol. 26.
Sadri et al., "Rapid analysis of DNA methylation using new restriction enzyme sites created by bisulfate modification," Nucleic Acids Research, 1996, pp. 5058-5059, vol. 24, No. 24.
Schorderet et al., "Analysis of CpG suppression in methylated and nonmethylated species," The Proceedings of the National Academy of Sciences, Feb. 1992, pp. 957-981, vol. 89.
Singer-Sam et al., "A quantitative HpaII-PCR assay to measure methylation of DNA from a small number of cells," Nucleic Acids Research, 1990, pp. 687, vol. 18, No. 3.
Singer-Sam et al., "A Sensitive, Quantitative Assay for Measurement of Allele-specific Transcripts Differing by a Single Nucleotide," PCR Methods and Applications, Feb. 1992, pp. 160-183, vol. 1, No. 3.
Swan et al., "A Sensitive, Type-Specific, Fluorogenic Probe Assay for Detection of Human Papillomavirus DNA," Journal of Clinical Microbiology, 1997, pp. 886-891, vol. 35.
Szabó et al., Allele-specific expression and total expression levels of imprinted genes during early mouse development: implications for imprinting mechanisms, Genes & Development, 1995, pp. 3097-3108, vol. 9.
Taylor et al., "Ultradeep Bisulfite Sequencing Analysis of DNA Methylation Patterns in Multiple Gene Promoters by 454 Sequencing," Cancer Research, 2007, pp. 8511-8518, vol. 67.
Thibodeau et al., "Microsatellite Instability in Cancer of the Proximal Colon," Science, May 7, 1993, pp. 816-819, vol. 260, No. 5109.
Thorsen et al., "Microfluidic Large-Scale Integration," Science, 2002, pp. 580-584, vol. 298.

(56) References Cited

OTHER PUBLICATIONS

Trinh et al., "DNA Methylation Analysis by MethyLight Technology," Methods, 2001, pp. 456-462, vol. 25.

Tyagi et al., "Molecular Beacons: Probes that Fluoresce upon Hybridization," Nature Biotechnology, 1996, pp. 303-308olume 14.

Tyagi et al., "Multicolor molecular beacons for allele discrimination," Nature Biotechnology, 1998, pp. 49-53, vol. 16.

Ushijima et al., "Establishment of methylation-sensitive-representational difference analysis and isolation of hypo- and hypermethylated genomic fragments in mouse liver tumors," The Proceedings of the National Academy of Sciences, Mar. 1997, pp. 2284-2289, vol. 94.

Veigl et al., "Biallelic inactivation of hMLH1 by epigenetic gene silencing, a novel mechanism causing human MSI cancers," The Proceedings of the National Academy of Sciences, Jul. 1998, pp. 8698-8702, vol. 95.

Vogelstein et al., "Digital PCR," The Proceedings of the National Academy of Sciences, 1999, pp. 9236-9241, vol. 96.

Warnecke et al., "Detection and measurement of PCR bias in quantitative methylation analysis of bisulfite-treated DNA," Nucleic Acids Research, 1997, pp. 4422-4426, vol. 25, No. 21.

Weisenberger et al., "Analysis of repetitive element DNA methylation by MethyLight," Nucleic Acids Research, 2005, pp. 6823-6836, vol. 33.

Weisenberger et al., "CpG island methylator phenotype underlies sporadic microsatellite instability and is tightly associated with BRAF mutation in colorectal cancer," Nature Genetics, 2006, pp. 787-793, vol. 38.

Widschwendter et al., "Association of Breast Cancer DNA Methylation Profiles with Hormone Receptor Status and Response to Tamoxifen," Cancer Research, 2004, pp. 3807-3813, vol. 64.

Wolff et al., Analysis of Chromosome 22 Deletions in Neurofibromatosis Type 2-related Tumors, American Journal of Human Genetics, Sep. 1992, pp. 478-485, vol. 51, No. 3.

Xiong et al., "COBRA: a sensitive and quantitative DNA methylation assay," Nucleic Acids Research, 1997, pp. 2532-2534, vol. 25, No. 12.

Zeschnigk et al., "A Single-Tube PCR Test for the Diagnosis of Angelman and Prader-Willi Syndrome Based on Allelic Methylation Differences at the SNRPN Locus," European Journal of Human Genetics, 1997, pp. 94-98, vol. 5.

* cited by examiner

SEQUENCE LISTING

<160> NUMBER OF SEQ ID NOS: 20

<210> SEQ ID NO 1
<211> LENGTH: 17
<212> TYPE: DNA
<213> ORGANISM: Artificial Sequence
<220> FEATURE:
<223> OTHER INFORMATION: PITX2 forward oligonucleotide primer 5' - 3'

<400> SEQUENCE: 1
agttcggttg cgcggtt                                                  17

<210> SEQ ID NO 2
<211> LENGTH: 22
<212> TYPE: DNA
<213> ORGANISM: Artificial Sequence
<220> FEATURE:
<223> OTHER INFORMATION: PITX2 reverse oligonucleotide primer 5'-3'

<400> SEQUENCE: 2
tacttccctc ccctacctcg tt                                            22

<210> SEQ ID NO 3
<211> LENGTH: 20
<212> TYPE: DNA
<213> ORGANISM: Artificial Sequence
<220> FEATURE:
<223> OTHER INFORMATION: PITX2 oligonucleotide probe 5' 6FAM - 3' BHQ-1

<400> SEQUENCE: 3
cgacgctcgc ccgaacgcta                                               20

<210> SEQ ID NO 4
<211> LENGTH: 29
<212> TYPE: DNA
<213> ORGANISM: Artificial Sequence
<220> FEATURE:
<223> OTHER INFORMATION: MLH1 forward oligonucletide primer 5' - 3'

<400> SEQUENCE: 4
gattggtatt taagttgttt aattaatag                                     29

<210> SEQ ID NO 5
<211> LENGTH: 28
<212> TYPE: DNA
<213> ORGANISM: Artificial Sequence
<220> FEATURE:
<223> OTHER INFORMATION: MLH1 reverse oligonucleotide primer 5' - 3'

<400> SEQUENCE: 5
caatcatctc tttaataaca ttaactaa                                      28

<210> SEQ ID NO 6
<211> LENGTH: 26
<212> TYPE: DNA
<213> ORGANISM: Artificial Sequence
<220> FEATURE:
<223> OTHER INFORMATION: Sequencing primer for MLH1 clones

<400> SEQUENCE: 6
gttattgttg tttaattaat agttgt                                        26

<210> SEQ ID NO 7
<211> LENGTH: 26
<212> TYPE: DNA
<213> ORGANISM: Artificial Sequence
<220> FEATURE:
<223> OTHER INFORMATION: C-LESS forward oligonucleotide primer 5' - 3'

<400> SEQUENCE: 7
ttgtatgtat gtgagtgtgg gagaga                                        26

<210> SEQ ID NO 8
<211> LENGTH: 22
<212> TYPE: DNA
<213> ORGANISM: Artificial Sequence
<220> FEATURE:
<223> OTHER INFORMATION: C-LESS reverse oligonucleotide primer 5' - 3'

<400> SEQUENCE: 8
tttcttccac cccttctctt cc                                            22

<210> SEQ ID NO 9
<211> LENGTH: 18
<212> TYPE: DNA
<213> ORGANISM: Artificial Sequence
<220> FEATURE:
<223> OTHER INFORMATION: C-LESS oligonucleotide probe 5' 6FAM - 3' BHQ-1

<400> SEQUENCE: 9
ctccccctct aactctat                                                 18

<210> SEQ ID NO 10
<211> LENGTH: 15
<212> TYPE: DNA
<213> ORGANISM: Artificial Sequence
<220> FEATURE:
<223> OTHER INFORMATION: CLDN5 forward oligonucleotide primer 5' - 3'

<400> SEQUENCE: 10
tgagggcgcg ggatc                                                    15

<210> SEQ ID NO 11
<211> LENGTH: 23
<212> TYPE: DNA
<213> ORGANISM: Artificial Sequence
<220> FEATURE:
<223> OTHER INFORMATION: CLDN5 reverse oligonucleotide primer 5' - 3'

<400> SEQUENCE: 11
cctaaaccaa cccaaaatac gct                                           23

<210> SEQ ID NO 12
<211> LENGTH: 28
<212> TYPE: DNA
<213> ORGANISM: Artificial Sequence
<220> FEATURE:
<223> OTHER INFORMATION: CLDN5 oligonucleotide probe 5' 6FAM - 3'
      BHQ-1-3

<400> SEQUENCE: 12
cgaccgcgac taaaacaacg acgaataa                                      28

<210> SEQ ID NO 13
<211> LENGTH: 21
<212> TYPE: DNA
<213> ORGANISM: Artificial Sequence
<220> FEATURE:
<223> OTHER INFORMATION: FOXE1 forward oligonucleotide primer 5' - 3'

<400> SEQUENCE: 13
gggttagttc gcgacgattt t                                             21

<210> SEQ ID NO 14
<211> LENGTH: 18
<212> TYPE: DNA
<213> ORGANISM: Artificial Sequence
<220> FEATURE:
<223> OTHER INFORMATION: FOXE1 reverse oligonucleotide primer 5' - 3'

<400> SEQUENCE: 14
cgaacctaac gtccccga                                                18

<210> SEQ ID NO 15
<211> LENGTH: 28
<212> TYPE: DNA
<213> ORGANISM: Artificial Sequence
<220> FEATURE:
<223> OTHER INFORMATION: FOXE1 oligonucleotide probe 5' 6FAM - 3'
      BHQ-1-3

<400> SEQUENCE: 15
cgaacgctcg acccttctac gaaaaact                                     28

<210> SEQ ID NO 16
<211> LENGTH: 1993
<212> TYPE: DNA
<213> ORGANISM: Homo sapiens

<400> SEQUENCE: 16
acaggtggga gagagttcaa accatttact aagcagattc ttagccttcc cactcccgcc     60
ctctctcaag ctccggtgcc cacaagcctt gcctggggag atgctggagt gagaccggga    120
ggtccaggcc aagtcactgg tccctgggct cgggccctgc cgatggagta aagaccagct    180
gtacacatct tccggtgggg gcctgggct ctgcatccgc cctccgaag tcagcaggag      240 cctctgggaa gtaaggcagc agccaagacc cccagcgtct tggaggggaa gcgaaatcct    300
cagtctgaca cccgctctgc ctatggaaac agcgccgcg acagaaaagg aaacttcatt     360
ccgtctgtta agggcagggc cgggctagtg gcaggagaag gtcagctgcg ggcgcaggca    420
ggagcggatc caggagccgc gtcggggcgc agagccggac gttccgagga gcctgcgcgc    480
cgcgctaccc ggcggaagcc gcggtccatg cggggctccc caggcttatc caacgcctcg    540
caggcgtggc tggcaggagg ggccggccg tgcccagcgc cctcagacgt agttcttctt     600
gtcgtagtcg ccggtggccg tgggccgccg cggcgctgag tacttcacgg ggaagctgag    660
gtcgggacgg ccggtgcaga cccaggcgcc gcagcacaag aggcagccgc ctaccatgag    720
cagcgcggtg gccgcccagc cgatgtacag cgctgcgccc agctcgtact tctgcgacac    780
gggcacagac gggtcgtaaa actcgcggac gacaatgttg gcgaaccagc agagtggcac    840
gagcgccagc agcccgcaaa acaggtagag cacgcctccc gtgagggcca cacgcgcctt    900
ggccgggccc ggggcacgc aggtggtgca ctgcgcgccc gccagggtca cgaagagcgc    960
aacgaacgcc agcagcacgg cgctcacggt gagcgcccgc gccgcctgca cctcggtgct   1020
cagagccagc accgagtcgt acactttgca ctgcatgtgc ccggtgctct gcaccacgca   1080
cgacatccac agcccttcc agtggtctg cgccgtcacg atgttgtggt ccaggaaggc    1140
ggtcacctgc cacatgggca gccgcacgc caggatcaga ccccccagc ccaccaggca    1200 cagcaccagg cccaggatct ccaacgctgc ggaccccatg gctagaggcg agacgcgcac   1260
ccgaaggccc gcagaacccc caaggccgtg ctgcgcggcg ccctgggcgg gcctggtgc    1320 cttgcgcccc gcgctcccgg ctcttggccc cagtccgttt gccccgcggg tctgtcgcac   1380

```
ctcctgggtc tgccagctcc tgccgggggg taccctcttt gaaggttcgg gggcggattc    1440 tgtccccgg  gcccggcccc ccggcccgaa gcagccaatc cgtgcgcggg tcatcgtgcc     1500
gcagccaatc acagagcctc tggcagctga agttagggaa caacggctc  ttgaggggta    1560 gctgagggcg cgggaccgct ccccgcccgg cagccgcccc cagccccacc cgccgttgtc    1620
ctagtcgcgg ccgagcgcat tctgggctgg cctagggcgc gcttcttggg ccgcctccct    1680
gcgcgtcccg gccccgtcac ttcagaaggc gctcgacccc cagtctgcac acccagtcc    1740 actcccacat ccccgactga gccgggtggt ctcttccact cgagccagct ccacttccct    1800
gaccaaggtt tgcagaagcc ccccaccccg tcaccgccgt agaggcctc  gtagggggc     1860 tctccagaaa gcccgccccg ggtccaagc  ccacccagg  ccctttctcg cactctcact    1920
ctccagcccc gctctgagtc ccagcactgt ctctctcatc ccatggcaaa cagagaggcc    1980
aggcaggcgt gtg                                                       1993

<210> SEQ ID NO 17
<211> LENGTH: 2960
<212> TYPE: DNA
<213> ORGANISM: Homo sapiens

<400> SEQUENCE: 17
aaagggaaag cggctacctc taccacacag ttgggaagcg cagtcctaaa ggagacgcag      60
gttggagact ccgctaagcg gagaagccgc agtggggcca tggcaagtca ccttcccttt    120
cgggcctagg aatactcatt cgaaagatgg ggggactgga gtgccgagtg gctgtggcag    180
ccacgattgg ggtttggaaa ccatcctgaa aggcccgggg agccagtctc ctggaacttc    240
tccctcccca ttcccacaaa aaccaagcgc cctctcggcc aattctcacc ctctcaggac    300
aaaaaagtga gatgagcccg tcctttcacc tgcgagtcca agcccttggc agaggcctga    360
aaagtccgaa aactccgagt tcgggcgctg aggtctcccg agccggttcc tgaactctcc    420
gggcctcagt cgatcggggt gcggaggggg ccgacccggg ggatctccaa gcgccctccc    480
cgccctgacg ctgtgggct  cctaccgcgc cgccacagct gctcctacct ggggaggtgc    540
gcccgggccc cggggggcgg gcagtcgggg ggcgggcagg gaaccggtgc cgccccacgc    600
ttcgtggccc cttttaaggag gggaagccgg cggaggagg  agccggtccg gtgtgtgcag    660
gggagcgcct cgccagcgt  ccgcagggct ggagacccac gccgtggaga ggaccagcct    720
caggtcgccc cgcctgggcc cgcgccccga cctcgctgcc cccgcctcgc ctctctgccc    780
gtggcgctta cggccacctt ggcctcgggg cagggcatg  ggcggccccc gccagatcgc    840
ccagcgccag tactaactgc cctcgctctg gccttcgagc ccgaagcctc ttctgcgcgc    900
acaacctagg cagtaatcct aaactagcgg gcaccacaga ccagctgcag ccaccccaac    960
ccagggatca cttccggacc cctcgaccgc ccggcaccag cgcgcaaggg accctttcagc   1020 cggagaccag agtccagtcc cggtcacgag gccaccgccg ctgcccgcct cgagaagcac   1080
cacgcgggct gagccgtcgg ctagcgggtc actcccgagc ctctgtctgc accgcgccag   1140
ccccagacca cggacgctga gcctccagcc cgtgccagcc tgggccgctg ggctctcggg   1200
gccagcccgc gacgatcccc tgagctctcc gcagaagggc cgagcgtccg ttccggggac   1260
gccaggcccg ccccgccccc cgacagccg  cggggatcca gagcccgggg gtgcgggacg   1320
cccgcgccat gactgccgag agcgggccg  cgccgccgca gccggaggtg ctggctaccg   1380
tgaaggaaga gcgcggcgag acggcagcag gggccggggt cccaggggag gccacgggcc   1440
```

-continued

```
gcggggcggg cgggcggcgc cgcaagcgcc ccctgcagcg cgggaagccg ccctacagct    1500
acatcgcgct catcgccatg gccatcgcgc acgcgcccga gcgccgcctc acgctgggcg    1560
gcatctacaa gttcatcacc gagcgcttcc ccttctaccg cgacaacccc aaaaagtggc    1620
agaacagcat ccgccacaac ctcacactca acgactgctt cctcaagatc ccgcgcgagg    1680
ccggccgccc gggtaagggc aactactggg cgcttgaccc caacgcggag gacatgttcg    1740
agagcggcag cttcctgcgc cgccgcaagc gcttcaagcg ctcggacctc tccacctacc    1800
cggcttacat gcacgacgcg gcggctgccg cagccgccgc cgccgccgcc gccgccgccg    1860
ccgccatctt cccaggcgcg gtgcccgccg cgcgcccccc ctacccgggc gccgtctatg    1920
caggctacgc gccgccgtcg ctggccgcgc cgcctccagt tactaccccc gcggcgtcgc    1980
ccggcccttg ccgcgtcttc ggcctggttc ctgagcggcc gctcagccca gagctggggc    2040
ccgcaccgtc ggggcccggc ggctcttgcg cctttgcctc cgccggcgcc cccgctacca    2100
ccaccggcta ccagcccgca ggctgcaccg gggcccggcc ggccaacccc tccgcctatg    2160
cggctgccta cgcgggcccc gacggcgcgt acccgcaggg cgccggcagt gcgatctttg    2220
ccgctgctgg ccgcctggcg ggacccgctt cgccccagc gggcggcagc agtggcggcg    2280
tggagaccac ggtggacttc tacgggcgca cgtcgcccgg ccagttcgga gcgctgggag    2340
cctgctacaa ccctggcggg cagctcggag gggccagtgc aggcgcctac catgctcgcc    2400
atgctgccgc ttatcccggt gggatagatc ggttcgtgtc cgccatgtga gccagcgtag    2460
ggacgaaaac tcatagacac atcggctgtt cacacgttcc ccgcaatctg agaacgaaca    2520
ggaatggaga gaggactcaa ctgggaccca cgtggaaaag accgagcagg ccacagaggc    2580
tcggtctccc cgcgcacagc gtaggcaccc ggtgtactct gtaaacggga ggaggtgggg    2640
cgaggcagcc agagcccttg gactggcaca gggaccctcg atggagcgaa gccctcaaac    2700
gggatgcttt ctggtattct atcggggagg gtccttggcg gtaaccagag ggcagcgtag    2760
tgtcaacacc agagaccagg atccaaattg tggggaatca gtttcagcct tccatgtgct    2820
gccggaactc gggccttttt acgcggttcg tcctctagtg cctttaactg cgttactaca    2880
ataaaaggct gcggcagcgc ctttcttctt aaagtgagga ggacaaattt gcaaagaaa    2940 taggcttttc ttctttttta                                                2960
```

<210> SEQ ID NO 18
<211> LENGTH: 4313
<212> TYPE: DNA
<213> ORGANISM: Homo sapiens
<400> SEQUENCE: 18

```
ttaatttcaa agactccttt taagctccaa gtgacagtaa aacctccgat ctgacgatta     60
aagtcacacg ggcctcccgc ccctcccggc gagatttccc ccactggtat tttaagatgt    120
cacccgggag acctcaaaga gccactcttc cttttttttcc catttagagt cgtcttaatg    180
ggagcaggga cggcctcagc ttccagccac ctcgggcagc accaccccca gccgccggcc    240
cttcctgccc tgccctttc tcacggcagc tgtgagaggt ttaggggaaa accgaggcgt    300
tttcgtttca tctcgctgcc cccttaaaaa aatgaaaatg aaacagtcgc ctactccctg    360
gcataaagaa aaaggtcctc taaatggctg ggggctgcca gggttagggg tcccccaatc    420
tcaactcgcc attcgggacg cataatatcc ccgagcaaac gtctggagag cagtgccccg    480
atcccggcct agcgccgtcc ggtaaaattt cggaagcccg agggtgtgag caggaagctt    540
ttgcgaagcg gcgcgggagg agggggtgctg gaggcggagg gtaggcccctt tcaccgttcg    600
```

```
caccccaccc gcggtgtcct tgccctgtc ccgggatcct cttctccgtt acccgcaggg    660
ctgtatctga gcgatccggg ttaggggggc gcaaaacccc atccgcccat ttccgcacca    720
acgtctctac gcaaggcgcc ccaaaaccca ggtggagcgg ggcaacccg ttaaaagtca    780
ttcctgcagg gcgcatccaa aacgaacgc cgaggtcccg gagccgagcg cgcagccaga    840
ctgaaccggg tgcccgggtg tcgccgcggc gtctcgggca cctcccatcc ccactgctcc    900
cgaggctctg gctcccgcag ctcagacgcc cggagcccca gggccggcgc cctcccgccc    960
cgggtcccgc actcaccttg aaggcgacgg gcagcgtctt gttgcagcgc cagtgcgagg   1020
gcagcacgga gcagaggaag ttggggctgt cggtgcgcac gagctcgcct gcgtggtccg   1080
ccagcacgtc caccatcgag cgcacctcgg gccgggcgcg ccctccgggc ccacggccg    1140
cctgcgcgct cagcgcgccg ctgttctcgc ccatcttgcc gccgccgccg ccgcagggga   1200
aggccgggga gggaggtgtg aagcggcggc tggtgcttgg gtctacggga atacgcataa   1260
cagcggccgt cagggcgccg ggcaggcgga cggcgcgg cttccccgg gggcggccgg    1320
cgcgggcgcc tcctcggccg ccgctgccgc gagaagcggg aaagcagaag cggcggggcc   1380
cgggcctcag ggcgcagggg gcggcgcccg gccactactc gccagggccc gcccgctgcg   1440
aggcctcgct ggcccgacgg ccgcccgcag cctgcccggc tagtcccgca tcctcggcgc   1500
gcggccccgc gtgcggccgc ccctcgtggc tgtcccggct gcctgggccg cggcggggcc   1560
cgcgcggggc tgtgccgctg ccgccgcctc ccgccccgaa gctcgcccgc ggccgccccg   1620
actccgcggc cgcagcccca gaacaaatcc tccagaatca agtggcgggg ccgcggccgc   1680
ccgcgcgggg ttagtacccc cggggcccgc ggggcggggc tggcggagcg acgcgtcgca   1740
cagccaatcg gcgagcccc catcgcgggc acctcggtgg cgttcgcggg gaggaacggg   1800
gcctgccgga ggccgcccaa cggggagggg cggaaggcgc caccccgcgg aggaggcccc   1860
agtgccacag cccagggccc ccgagagctc tgggagcccg gggcaaatgc tagaaatttg   1920
cttagaacgt ccgggtccca cggaaggcgc ccttgccgcc ctctctcggg tcgtagctcc   1980
ctgacgctgg ggcgcaaccc cttcgctcct cctcccccgct ggccgcgcgcc gggcttcccc   2040
agctcttgct gcttcgggcc tgtgacttct gcaaccccgg gctgggggcc gcggggtctc   2100
agggccggtg acgccgcact gggagccgcc ccaaagaggt tactcacctc cctcgtcccg   2160
cacattattc tgacccaaga gcctccaccc cacacgggat tttgcgcgtc gtccacgccc   2220
ggccggcggc ctttgctgct cccagccctg cgcggctttg gtcccagcct cggtggcccc   2280
tgtgccaaac cggggacagg cggaagggag tctcctaggg accctaagta gcctggggcc   2340
aacaacccct ttcctctctg ctctcccctc aaaacaagtt tcaggatctt gcaggcctcg   2400
cggcgtcgtt cttcgttgtg gcggcctgtg gctctttgaa aaacgacg aggcctgcaa    2460
aatgcgtttt tcttttttc ctttacgcat gtaaccacgg tcctgcatcg tgaaacggta   2520
cgcgcgtcgg tggcaaaaga aaaacagcag tggctgcaaa gctaagggcc ctcgctttca   2580
gaggagagaa ttttctttct ccatgcgggt ggaaagtggc ctctgcgggt ccaaccccac   2640
ttcttcttgg gcccgtgcgc tccggctgcg ccgcagggac cgcggacagc ttcgccaagg   2700
cactgcctgc ccgcccggct ccgggtcccc gctcccactc ccagccgcgt ggcccaacct   2760
ctcctgggct tcactgcaaa tcacccttc ctctccccgcc tcctaagtct gtcgagcaga   2820
cctaggggcc ggctacagtt gggagggcaa cggaaaagat caagccacaa tcattccgaa   2880
ttatcgcccc agacacctcc ctagactctg gggaacgaac gcgtgctgag cctccccgcc   2940
```

```
gctttggaga cggggctaga ttttcgttgc ctccggctct cgacaggtgc aaaacaatga    3000
attccaagcc tcggaagcaa agaagcttag gatccgacgg tggccgcaag atctcatcat    3060
ggatctgacc cctgctcagc gcgcgccatt tcgtcgttgc caaacgaaat caagccccgc    3120
gtgcgctcca ggggcgaagg actctggact caccccgacc accggagag  ctggcccta    3180 cccacctcgg gacctcacag cacgccctca ggccgtgtcg aaaggaagga cggcaaaggt    3240
cccttactga acctttaag  agagcctgcg cctggcagtt gtcgattgcg gacccaggcc    3300
cgcgcgccct cggacgcgct ggcacgagca gcagaactag aggaaagcga gtgatccagc    3360
ctgggcgctc ccacctccgg gaacgtctcc gagaaggcgc agcgcgtcgt ggccaggtag    3420
ggccctggcc gggggcgggc aacacgtgct gccctcgagc aggttgcggg accatgaccc    3480
gctgtttcag gtggtggtaa attccatttg tcgaatggtt tcggtttgca ccgtgcccctt   3540 tgcttgttcc tccgcctgat ttctcccctct ccgcttacga tgggttcaca gacaagtttc   3600
cagagaatga gggactcttg tgggccctgg cacctggcgc agggcccggc acggctccgg    3660
ctctccgtag ggcgctggct ccccgtgggc accagatcca agggaccagg gcggcggggg    3720
gagggggggc gggtgcaggc ccttgggtcc ccagaccaag gtcgcggggc cgcctggcag    3780
gcacagtggc gggagccgcc gctagttggc gcccgcgccc tgccagccgc ggaggtgcgg    3840
gcccggccgg gctacagatg cgcgccagct gcggccccgg gtgcaggcgc ggcgaccgcc    3900
cccgaggagc tgcccttttcc ttgccatcca tgcggccagg tctcagacaa accgatggct    3960
ttgtgtcaaa ccaaggccgc cttcctcacc tctgataaga tggacgcctt ctgtcttcgc    4020
gttttcaggc acccggggaa gacccacaga acaggctagc ttgttcccaa tttccacctg    4080
cttcctcccc atcccggacc gacaaaaatt gtcgtctgtt tgatgggagg gagaactccg    4140 actccccccac ctggggcatg cagacaccct cgcccttccc cagttggcat ggaccgtcgt    4200
cttttctccc tcttccatca gatcgatgga caaacaggcc agtttctccc cagtggcccc    4260
cacctaagag caccctaagt tgtccacagc agggctagga agcagaaggt cag           4313
```

<210> SEQ ID NO 19
<211> LENGTH: 1749
<212> TYPE: DNA
<213> ORGANISM: Homo sapiens

<400> SEQUENCE: 19

```
atggataaca atgggaaggg ggctaatctt ccagtagctg aaactttgta cccagccctt      60
tatcttgaga tgctaatcc  ttggcccgag gatttgttcc tgcagtgttg gcaccgagat     120
ttaagggaag ataccctcgtt ttaaatgcca gccacggtct ggcttccctc tcgacttcag    180
caccctgtag attgttagtg tctgtggcgg gggacgaaag gaacagggct ttgcaaggtc     240
tgtttgccga ctgcgttacc ttgggcgaaa cttagcccca aaagccacaa atcacctacg     300
gtgaagattc tccgaagtgg aacaaatttc cagactcgca ttatctcaca tccctgcggg     360
atagatggcc tccacttacc ggctaccggg agagagctg  tgtctccgcg tcccactgct     420
tcccggggcg atttccagcg agccgagcct ccggctgcac ggcaagcgcc cgaaagccgg     480
gcctgagagg actgcagggc tcctgagggt gccaagttcc gaaggagtcc acgggtgcac     540
tggggcctcc gaaatctagc cgccactggc agtttctttc tgctcctctc cagctttctc     600
gctcggtctc gcactctctc tcctctccct ccctctcatc cctctctctt ccctctgctc     660
ctactccgtg tggggagtga cgtgacgtca gcagagattc caccaaactc cactgcacag     720
tggcgcgcgg gcggccggcc gagcccggct gcgcggctgg cgatccagga gcgagcacag     780
```

```
cgcccgggcg agcgccgggg ggagcgagca ggggcgacga gaaacgaggc aggggaggga        840
agcagatgcc agcgggccga agagtcggga gccggagccg ggagagcgaa aggagagggg        900
acctggcggg gcacttagga gccaaccgag gagcaggagc acggactccc actgtggaaa        960
ggaggaccag aagggaggat gggatggaag agaagaaaaa gcaatctgcg ccaacccggc       1020
agccctaata aatcaaaggg ggagcgccag ggcagcgggg agacagaaac gtacttttgg       1080
ggagcaaatc aggacgggct gggaggaagc gacagggaaa gtgcccaag agacggaaca       1140 aaggacaatg ttcatggggt tgtttgggac gaggcgtgtg gagtgtgggt gtgagcgtgc       1200
gtgtgtgacc ttctttcagg cctgcagagt tgaggaaaga ggtcacagca aagagggact       1260
gcggagggag gaaagtgaga gaccggtaga gggcgggagt ggaggtgggc gcggtgggga       1320
tgggagagga tgagtgaaga gaaatctaga agaatggagt gagctagtgg gagagggtgg       1380
gagggccaca gccgggagcg aacgagctag gcttgtcagc tggggaaggc cgggacgctg       1440
ggcccagctt agctgggaca ccgcgcccga ggtcaaggcg ggtggaccag gcatgctgag       1500
agtgtcggcg cacaggtggg cacggccacg cactgaccca gtgttcacga agggtttgca       1560
ctggacaagg ctcagacgct catagagtct agaatttcct ctgctgtacc tacattcaac       1620
aagttcaccc tgggtcacgg atatctcatt ttttaaaatg acgaggttaa ggttcctggc       1680
gaggatggta ttaaattgca cgggatagaa gtgggggtgg gggagagagt ttccctcaag       1740
tccacattt                                                               1749

<210> SEQ ID NO 20
<211> LENGTH: 1396
<212> TYPE: DNA
<213> ORGANISM: Homo sapiens

<400> SEQUENCE: 20
aaaaagctgg ttgcgtagat tcctgtcaat gctcaggatc ctctgccttg tgatatctgg         60
agataagtca acgccttgca ggacgcttac atgctcgggc agtacctctc tcagcaacac        120
ctccatgcac tggtatacaa agtccccctc accccagccg cgaccccttca aggccaagag       180 gcggcagagc ccgaggcctg cacgagcagc tctctcttca ggagtgaagg aggccacggg       240
caagtcgccc tgacgcagac gctccaccag ggccgcgcgc tcgccgtccg ccacataccg       300
ctcgtagtat tcgtgctcag cctcgtagtg gcgcctgacg tcgcgttcgc gggtagctac       360
gatgaggcgg cgacagacca ggcacagggc cccatcgccc tccggaggct ccaccaccaa       420
ataacgctgg gtccactcgg gccggaaaac tagagcctcg tcgacttcca tcttgcttct       480
tttgggcgtc atccacattc tgcgggaggc cacaagagca gggccaacgt tagaaaggcc       540 gcaagggag aggaggagcc tgagaagcgc caagcacctc ctccgctctg cgccagatca       600
cctcagcaga ggcacacaag cccggttccg gcatctctgc tcctattggc tggatatttc       660
gtattccccg agctcctaaa aacgaaccaa taggaagagc ggacagcgat ctctaacgcg       720
caagcgcata tccttctagg tagcgggcag tagccgcttc agggagggac gaagagaccc       780
agcaacccac agagttgaga aatttgactg gcattcaagc tgtccaatca atagctgccg       840
ctgaagggtg gggctggatg gcgtaagcta cagctgaagg aagaacgtga gcacgaggca       900
ctgaggtgat tggctgaagg cacttccgtt gagcatctag acgtttcctt ggctcttctg       960
gcgccaaaat gtcgttcgtg gcaggggtta ttcggcggct ggacgagaca gtggtgaacc      1020
gcatcgcggc gggggaagtt atccagcggc cagctaatgc tatcaaagag atgattgaga      1080
```

-continued

```
actggtacgg agggagtcga gccgggctca cttaagggct acgacttaac gggccgcgtc   1140
actcaatggc gcggacacgc ctctttgccc gggcagaggc atgtacagcg catgcccaca   1200
acggcggagg ccgccgggtt ccctgacgtg ccagtcaggc cttctccttt tccgcagacc   1260
gtgtgtttct ttaccgctct cccccgagac cttttaaggg ttgtttggag tgtaagtgga   1320
ggaatatacg tagtgttgtc ttaatggtac cgttaactaa gtaaggaagc cacttaattt   1380
aaaattatgt atgcag                                                    1396
```

DNA METHYLATION ANALYSIS BY DIGITAL BISULFITE GENOMIC SEQUENCING AND DIGITAL METHYLIGHT

CROSS REFERENCE TO RELATED APPLICATION

This application claims the benefit of priority to U.S. Provisional Application Ser. No. 60/911,495, filed Apr. 12, 2007, which is incorporated herein by reference in its entirety.

REFERENCE TO FEDERALLY SPONSORED RESEARCH

This invention was made with government support under Contract No. R01 CA096958awarded by the National Institutes of Health. The government has certain rights in the invention.

FIELD OF THE INVENTION

Aspects of the invention relate generally to novel methods for sequencing and sensitive detection of aberrant DNA methylation, and more particularly to digital methods that are substantially more sensitive than prior methylation detection methods. Additional aspects relate to compositions and methods for diagnosis and/or prognosis of breast cancer, comprising the use of FOXE1 and/or CLDN5 gene markers, optionally in combination with RUNX3 gene markers in methylation assays.

BACKGROUND

Alterations of CpG island DNA hypermethylation and chromatin modification have been widely documented in human cancers (1,2). DNA methylation changes are not only detectable in tumors, but also in blood, as tumor-derived DNA is released into the bloodstream due to tumor necrosis and apoptosis (3,4). Cancer-specific DNA methylation alterations present in cancer tissues and blood of cancer patients can serve as diagnostic markers for risk assessment, progression, early detection, treatment prediction and monitoring (5).

The sensitive detection of specific DNA methylation patterns occurring at very low abundance presents technological challenges that are distinct from the challenges of determining the sequence of consecutive methylation states at single base-pair resolution in individual DNA molecules. The former requires high signal-to-noise ratio, and generally relies on methylation-specific PCR priming (MSP) (6), with optional further enhancement by methylation-specific probing (MethyLight) (7), whereas high-resolution sequencing requires low-sensitivity methylation-independent priming, combined with separation of PCR products for sequence analysis. This separation has traditionally been accomplished by a plasmid cloning step in E. coli prior to sequencing (8).

MethyLight is a quantitative, TaqMan-based real-time PCR assay for measuring methylation levels at a known CpG-containing DNA sequence using bisulfite-converted DNA as a substrate. A high specificity for methylated DNA is attained because both methylation-specific priming and probe annealing events are required to occur.

There is a pronounced need in the art for improved methods for bisulfite genomic sequencing. There is a pronounced need in the art for sensitive detection of aberrant DNA methylation in, for example, cancer patients. There is a pronounced need in the art for sensitive detection of aberrant DNA methylation to provide for improved cancer diagnosis and/or surveillance. There is a pronounced need in the art for novel methylation assay methods that have sufficient resolution to identify and quantify single methylated DNA molecules in a background of unmethylated or competitive genomic DNA.

SUMMARY OF EXEMPLARY ASPECTS

In particular aspects, Applicants have applied Digital PCR technology to two bisulfite-DNA based DNA methylation assays, Digital Bisulfite Genomic DNA Sequencing and Digital MethyLight, to obtain DNA methylation information at high resolution or with high sensitivity, respectively. Both Digital Bisulfite Genomic DNA sequencing and Digital MethyLight are novel, fast, reliable and cost effective measures for determining DNA methylation information of individual DNA molecules, and are easily customizable to the analysis of any gene region and sample type.

Particular aspects provide a novel methylation assay referred to herein as Digital MethyLight having substantially enhanced sensitivity relative to the prior art. Digital MethyLight provides a substantial improvement of the art-recognized MethyLight platform, and is capable of amplifying individual methylated DNA molecules in a background of unmethylated genomic DNA by compartmentalizing the PCR reaction over multiple reaction wells. In particular exemplary aspects, the increased methylated DNA detection sensitivity of Digital MethyLight has substantial utility in detecting abnormally methylated DNA molecules in blood-based tests. Digital MethyLight technology has substantial utility for the detection of methylated DNA molecules from biological fluids, such as serum, plasma and urine, which is important in the arena of cancer detection and surveillance. The technology can be implemented in numerous PCR-based assays, and can be used in multiplexed MethyLight assays to sensitively identify multiple methylated loci in a small amount of a DNA analyte.

Digital PCR (9) was originally described as a tool for the amplification of individual molecules for purposes of identifying and counting individual DNA molecule sequence alterations. By distributing a sample over multiple PCR reaction wells to a mean concentration well below one template molecule per well, amplification of single template molecules is achieved in a minority of the wells, providing a digital readout of the original number of template molecules in the distributed sample. Applicants have applied this principle to bisulfite genomic sequencing. By omitting the time- and labor-intensive cloning step in E. coli (8), Digital Bisulfite Genomic Sequencing greatly increases the efficiency of single-molecule DNA methylation analysis, and results in a significant cost reduction. PCR wells with positive amplification can be recognized by the use of SYBR Green, and sequencing can be performed directly on the PCR products following clean up. Thus, Digital PCR not only provides information on the number of discrete templates, but can also be used to separate heterogeneous templates into separate amplifications for subsequent sequencing. In additional aspects, a benefit of Digital PCR is the sequestration of competing background molecules into negative wells that do not participate in the PCR amplification. As a consequence, the ratio of template-to-background improves in the positive wells. Competition for primer annealing by background DNA is a major problem in the detection of low-abundance methylation variants by MSP and MethyLight. This problem is particularly acute for these bisulfite-based detection methods, since sequence redundancy is increased in bisulfite-converted DNA, which contains only three bases outside of sites of DNA methylation (10). This is not only the first application of Digital PCR to bisulfite-treated DNA, but also to methylation analysis, the methods are upredictably effective. The method is particularly beneficial for the analysis of biological fluids (e.g., blood, plasma or serum samples) containing relatively small amounts of DNA. As appreciated in the art, such samples, in the context of PCR assays, are typically associated with relatively high background signal levels, particularly where the ratio of primer to methylated template DNA is kept high to increase the signal level. Moreover, the situation of having a low abundance of methylated DNA in the samples is further exacerbated by virtue of the fact that methylation pattern and/or extent of methylation may vary at any given locus among or between individual DNA molecules, effectively further reducing the methylated substrate concentration.

DETAILED DESCRIPTION

Figure 1:
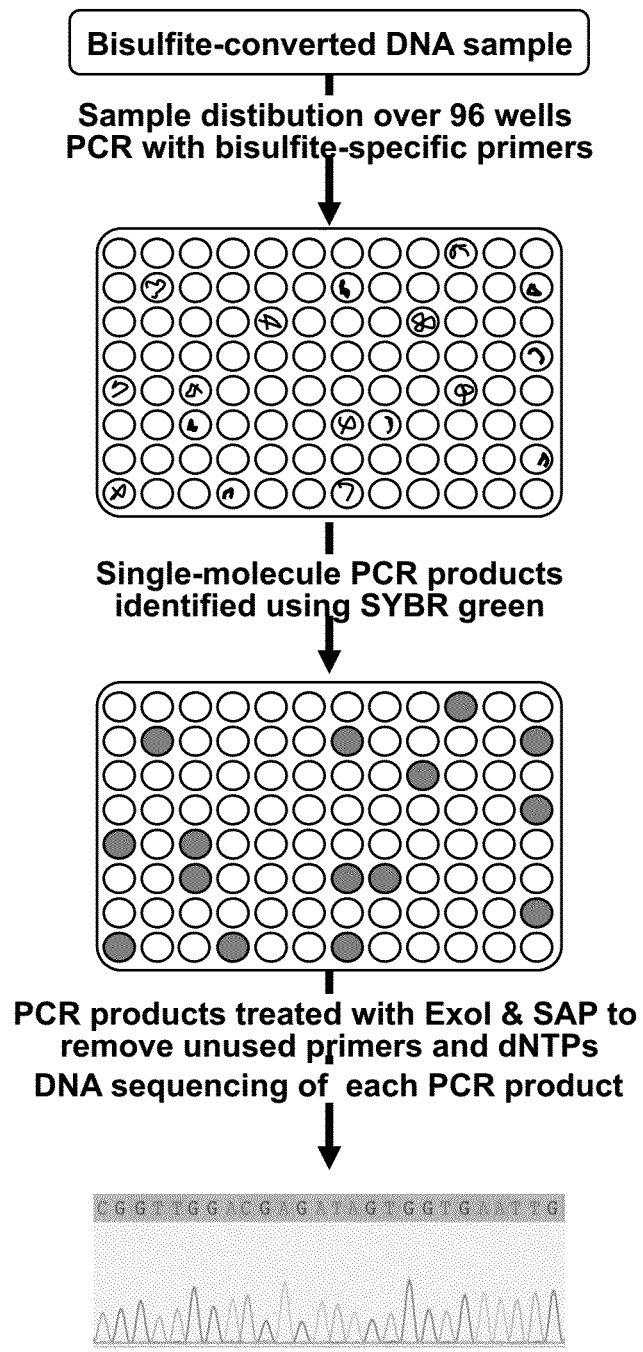
FIG. 1 shows, according to particular exemplary aspects, Digital Bisulfite Genomic DNA Sequencing Overview. Bisulfite-converted DNA was diluted such that approximately 20-30 DNA molecules were analyzed over a 96-well PCR plate. Positive amplifications are evaluated by SYBR green melting curve analyses, and PCR products from these wells are removed and purified with Exonuclease I and Shrimp Alkaline Phosphatase (Exo-SAP-IT) to remove unused PCR primers and dNTPs. PCR products representing individual DNA molecules are then subject to DNA sequencing.

Particular aspects provide novel advancements in single-molecule DNA methylation detection and bisulfite sequencing.

Particular aspects provide two novel DNA methylation analysis tools utilizing Digital PCR technology. Digital MethyLight allows for detection of individually methylated DNA molecules in a large background of unmethylated DNA, while Digital Bisulfite Genomic DNA Sequencing generates high-resolution DNA methylation information without the need for a subcloning step. Both assays are efficient and effective methods of obtaining DNA methylation information for samples with small amounts of DNA. Single-molecule analysis is possible by compartmentalizing the template across multiple PCR reaction wells. Not only are single molecules isolated, the background and other PCR contaminants are also diluted, and the ratio of primer to methylated template DNA is kept high.

Digital MethyLight and Digital Bisulfite Genomic DNA Sequencing are cost and time effective methods in which a wide range of samples and loci can be assayed.

Digital MethyLight:

Particular aspects of the present invention, herein referred to as Digital MethyLight, provide a substantial improvement of MethyLight technology (see EXAMPLE 3 and 4, herein). In Digital MethyLight applications, a MethyLight PCR reaction containing a bisulfite-converted DNA sample is compartmentalized over a 96-well reaction plate such that there is less than one methylated molecule per reaction well (FIG. 1a). After the PCR reaction is completed, the fluorescent peaks, indicative of the amplification of single methylated DNA molecules, are counted and the number of methylated molecules of a particular locus relative to a specific volume of plasma or serum, for example, can be determined. Since the bisulfite-convered DNA sample is compartmentalized over the entire reaction plate, the background non-tumor derived DNA content is also sequestered in different PCR reaction compartments from the ones containing the methylated DNA template molecules. In this scenario, the ratio of methylated template DNA relative to competitive DNA levels are improved while the primer/probe levels remain constant, and allows for the amplification of discreet methylated molecules. Previously, digital PCR methods were not known or considered suitable for assessment of DNA methylation, because of the background and contaminant levels in typical samples of Genomic DNA.

Digital MethyLight was shown to be significantly more sensitive than classic MethyLight in detecting a small number of methylated molecules in a large background of unmethylated DNA. Digital MethyLight, in compartmentalizing the methylated DNA molecules over multiple PCR wells, also reduces the background and contaminant levels, thereby reducing their PCR inhibitory effects and increasing methylated DNA detection sensitivity. This strategy allowed Applicants, for example, to detect and quantify the number of individual methylated DNA molecules in plasma samples of breast cancer patients. Digital MethyLight is the most sensitive assay described to date for detecting methylated DNA in biological fluids.

The additional refinement of multiplexing Digital MethyLight assays increased the sensitivity of detecting methylated DNA loci in plasma samples. Although the multiplexed assays detected DNA hypermethylation mostly in plasma from Stage IV breast cancer patients, Applicants' did detect DNA methylation in one stage II patient. In particular aspects, the method can be further improved by using an increased number of multiplexed MethyLight markers in each Digital MethyLight assay. Nonetheless, the CpG islands located in RUNX3, FOXE1, and CLDN5 (SEQ ID NOS: 18, 17 and 16, respectively) are promising DNA methylation markers for breast cancer patients. RUNX3 DNA methylation was previously shown in breast cancer patients (16), while FOXE1 and CLDN5 methylation in breast cancer has not been described previously.

In particular aspects, Applicants used an amount of DNA present in a small volume (100 µl) of serum for Digital MethyLight-based detection. A recent study (17) identified DNA methylation of SEPT9 in 70% of patients stage I-III colorectal cancer from triplicate measurements of a large volume (2 ml) of plasma. In additional aspects, while the amount of cancer patient plasma or serum is usually limiting for laboratory use, use of larger volumes of plasma or serum in Digital MethyLight assays increases the detection sensitivity of individual methylated DNA molecules. The early detection of methylated DNA in biological fluids using Digital MethyLight has great promise in cancer detection and surveillance.

Digital Bisulfite DNA Sequencing:

Applicants further provided Digital Bisulfite DNA Sequencing (see EXAMPLE 2 herein), which is a powerful method of amplifying individual bisulfite-converted DNA molecules for DNA sequencing. DNA methylation patterns of individual gene loci can be heterogeneous, and an understanding of the DNA methylation patterns of individual molecules may be helpful to determine the role of DNA methylation in gene regulation and the mechanism of DNA methylation at specific gene loci. Digital Bisulfite Genomic DNA Sequencing is a quick and efficient assay in which individual template DNA molecules can be amplified, screened, purified and sequenced in the same day. This assay is time and labor effective in comparison to subcloning techniques to isolate individual bisulfite-converted DNA molecules.

A recent study from Taylor et al (18) used 454 Sequencing technology to identify individual molecule CpG methylation patterns in lymphoma and leukemia primary cells. While this assay is robust and powerful in generating large amounts of bisulfite sequencing data, there are substantial equipment and informatics requirements for 454 and other next-generation DNA sequencing platforms. Although Digital Bisulfite Genomic DNA Sequencing does not generate the amount of sequence data compared to 454 Sequencing, only a real-time PCR machine is required and approximately 20-30 individual molecules can be quickly assayed and sequenced. High-resolution sequence information of 20-30 DNA molecules can provide a detailed understanding of DNA methylation events at candidate gene loci. Digital Bisulfite Genomic DNA Sequencing is an advantageous and flexible technology for determining single-molecule DNA methylation patterns of a wide range of DNA samples and gene loci.

Figure 4:
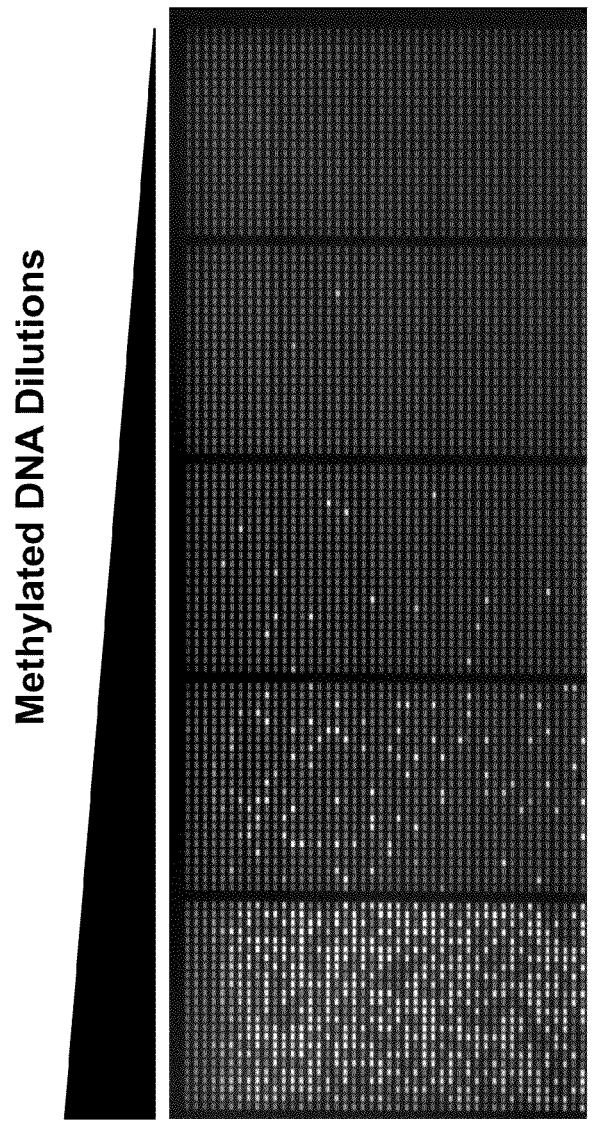
FIG. 4 shows, according to particular exemplary aspects, detection of single methylated PITX2 molecules serial dilutions of bisulfite-converted M.SssI-DNA using microfluidic Digital MethyLight (Fluidigm). Each DNA sample was compartmentalized into 1,104 reaction chambers of 10 nl each and amplifications were visualized by fluorescence emission in each positive chamber.

Diagnosis and/or Prognosis of Pancreatic Cancer and Breast Cancer:

Digital MethyLight was used to detect single methylated PITX2 molecules in sera of pancreatic cancer patients (see EXAMPLE 5, herein). Digital MethyLight was tested for its ability to detect single methylated PITX2 molecules in sera of pancreatic cancer patients. In particular aspects, microfluidic MethyLight was applied to serial dilutions of M.SssI-treated serum DNA samples from pancreatic cancer patients to amplify single methylated PITX2 molecules (FIG. 4).

Digital MethyLight technology was also tested on biological samples for the detection of tumor-derived, methylated DNA in the bloodstream (see EXAMPLE 6, herein). Digital MethyLight was applied to DNA isolated from plasma of 44 breast cancer patients of different stages of disease and 13 apparently normal individuals. MethyLight reactions specific for methylated CpG islands located in the promoter regions of FOXE1, CLDN5 and RUNX3 were selected for this analysis (SEQ ID NOS:17, 16 and 18, respectively). Using classic MethyLight, these reactions showed high cancer specificity in breast cancer tumor samples, and did not detect methylation in a test panel of plasma and white blood cells (WBC) from age-matched healthy control individuals (data not shown). As a result, these reactions would generate a low background signal from lysed WBCs and other free DNAs present in the breast cancer patient plasma samples.

EXAMPLE 1

Materials and Methods

Pancreatic Cancer:

DNA isolation from pancreatic tumor tissues and serum. Tumor DNA from nine pancreatic cancer patients was extracted as previously described (Weisenberger, D. J. et al. Analysis of repetitive element DNA methylation by MethyLight. *Nucleic Acids Res* 33, 6823-36 (2005)). Blood (10 ml) was also collected in clot tubes from each patient. A serum sample from an apparently healthy 65-year old woman was collected as a control. Blood samples for serum isolation were incubated at room temperature (RT) for 15 min to allow the blood to coagulate, and then centrifuged at 1,600 g for 10 min at RT. The serum was isolated and re-centrifuged under the same conditions to eliminate white blood cell contamination, and then aliquotted and stored at −80° C. DNA from 1.2 ml serum was then purified using the QIAamp Viral RNA Mini Kit (Qiagen, Valencia, Calif.) as previously described (Id) and the purified DNA samples were eluted in 120 µl volume. Each serum DNA sample was concentrated to 18 µl prior to bisulfite conversion.

Bisulfite conversion and recovery. DNA samples from pancreatic tissue (4 µg DNA), and serum from the nine pancreatic cancer patients (amount of DNA derived from 1.2 ml of serum which concentrated to 18 µl after DNA isolation to accommodate bisulfite conversion reaction) were treated with bisulfite as previously described (Id). For the two MethyLight marker pre-screens, we first bisulfite converted 4 µg pancreatic tumor DNA and then 2.8 µg serum DNA from the age-matched control. The purified bisulfite-converted samples were eluted in a 120 µl volume, and in order to remove traces of ethanol-based PCR inhibitors, we then incubated the samples at 80° C. for 20 minutes, and then stored the samples at −30° C.

MethyLight Analysis. Applicants prescreened 119 MethyLight reactions on the nine pancreatic tumor DNA samples and one serum DNA sample from an apparently healthy age-matched control. For the serum control, each reaction was assayed for the equivalent of 40 µl serum. The methylation values were expressed as PMR (percent of methylated reference) in which a DNA sample treated with M.SssI was used as a methylated reference, and ALU (Id) and COL2A1 reactions were used to control for bisulfite DNA input (Widschwendter, M. et al. Association of breast cancer DNA methylation profiles with hormone receptor status and response to tamoxifen. *Cancer Res* 64, 3807-13 (2004)). In order to identify candidate reactions that would have the greatest potential to detect tumor-specific methylation in serum, reactions were identified that gave the highest PMR values and methylation frequencies in the tumor tissue samples, concurrent with the absence of methylation in the control serum sample. The reactions that were positive in DNA from the control serum sample and/or did not show methylation in any of the tumor samples were eliminated. Another counter-screen of the remaining 48 MethyLight reactions was next performed using the equivalent of 0.1 ml serum per reaction, and any reaction that came up positive for methylation was eliminated. From these analyses, the MethyLight reaction specific for a CpG island in PITX2 gave an 89% methylation frequency (methylation positive samples had PMR values greater than zero) in the pancreatic cancer tissue samples, was not positive in the control serum sample and had a low C(t) value on M.SssI-treated DNA.

Digital MethyLight. Digital MethyLight was performed to count the number of methylated PITX2 molecules present in bisulfite-converted. Each bisulfite-converted DNA sample was mixed with 200 µM dNTPs, 0.3 µM forward and reverse PCR primers, 0.1 µM probe, 3.5 mM MgCl$_2$, 0.01% Tween-20, 0.05% gelatin and 50 units of Taq polymerase in a 2.85 ml total volume. The PITX2 MethyLight primers were obtained from BioSearch Technologies and are as follows: forward, 5'-AGT TCG GTT GCG CGG TT-3' (SEQ ID NO:1); reverse, 5'-TAC TTC CCT CCC CTA CCT CGT T-3' (SEQ ID NO:2); probe (5' to 3'), 6FAM-CGA CGC TCG CCC GAA CGC TA-BHQ-1 (SEQ ID NO:3). The entire reaction mixture was aliquotted over 94 wells (30 µl/well) in one 96-well plate. Two M.SssI samples were also included in each plate that contained 5 and 10 methylated DNA molecules as positive controls for each plate. For the M.SssI-DNA dilution series (FIG. 1b), M.SssI-DNA was diluted in serial 1:3 dilutions, and the MethyLight PCR reaction mixture was the same as above, except we used 16.67 units of Taq polymerase in a 0.96 ml total volume, which was distributed in 10 µl aliquots over 96 reaction wells. All Digital MethyLight PCR reactions were performed as follows: 95° C. for 10 min, then 50 cycles of 95° C. for 15 sec followed by 60° C. for 1 min. The reactions were analyzed on an Opticon DNA Engine Continuous Fluorescence Detector (MJ Research/Bio-Rad) and the number of positives for each sample was scored.

Microfluidic Digital MethyLight. Bisulfite-converted M.SssI-treated and serum DNAs were concentrated using art-recognize methods.

Colorectal Cancer:

M.SssI and Whole Genome Amplification (WGA) treatments. DNA was treated with M.SssI methylase (New England Biolabs, Ipswich, Mass.) or with Phi 29 DNA polymerase (Sigma) as previously described (11).

Bisulfite conversion and recovery. DNA samples were treated with bisulfite as previously described (11). The purified bisulfite-converted samples were eluted in a 120 µl volume, and in order to remove traces of ethanol-based PCR inhibitors, we then incubated the samples at 80° C. for 20 minutes, and then stored the samples at −30° C. until needed.

Digital Bisulfite Genomic DNA Sequencing. Tumor DNA from two colorectal cancer patients (Laird IDs 6317 and 6363) was bisulfite converted and recovered as described above. For the conventional, cloning-based bisulfite DNA sequencing approach, we amplified a portion of the MLH1 CpG island using forward (5'-GAT TGG TAT TTA AGT TGT TTA ATT AAT AG-3') (SEQ ID NO:4) and reverse (5'-CAA TCA TCT CTT TAA TAA CAT TAA CTA A-3') (SEQ ID NO:5) primers. The PCR was performed on a Robocycler (Stratagene) containing 200 µM dNTPs, 2 mM MgCl$_2$, 0.3 µM forward and reverse primers and 0.5 units of Taq polymerase. The PCR conditions are as follows: 95° C. for 3 min, then 35 cycles of 95° C. for 1 min, 55° C. for 1 min and 72° C. for one min. A final incubation at 72° C. for 15 min concluded the PCR. PCR products were verified by gel electrophoresis, and a small aliquot of the PCR reaction was used with the TOPO-TA cloning system (Invitrogen, Carlsbad, Calif.) as suggested by the manufacturer. Clones were picked from LB-Amp cultures, and then were screened and amplified using M13 primers as previously described (8). Positive clones were then sequenced using the following sequencing primer: 5'-GTT ATT GTT GTT TAA TTA ATA GTT GT-3' (SEQ ID NO:6) by the USC/Norris Cancer Center DNA Sequencing Core Facility.

For the Digital Bisulfite Genomic DNA sequencing assay, we first established the amount of bisulfite converted DNA to load on the 96-well PCR assay in order to avoid over- or under-loading the template DNA. To accomplish this, we determined the Ct value of each sample using the ALU control reaction described previously (11) sensitively measure bisulfite-DNA amounts. These Ct values were calibrated to the C-LESS signal using genomic DNA as a standard. We diluted each sample accordingly such that 20-30 DNA molecules were loaded into each Digital MethyLight assay. Each PCR reaction used the iQ SYBR Green Supermix (Bio-Rad, Hercules, Calif.) and 0.3 µM forward and primers in a 1.44 ml total volume. This volume was dispersed in 15 µl aliquots over an entire 96-well plate, and the PCR was performed using Opticon real-time thermal cycler (Bio-Rad) using the PCR program of 95° C. for 10 min, followed by 50 cycles of 95° C. for 15 sec and 55° C. for 1 min. Using a melting curve analysis, we identified the melting curve of the PCR product in each well. Primer dimers melted at approximately 70° C., while single-molecule PCR products melted between 77-85° C. We randomly chose true PCR products for sequencing. We removed 10 µl from each well, and removed unused dNTPs and primers using the ExoSAP-IT kit (USB Corporation, Cleveland, Ohio) according to the manufacturer's specifications. The MLH1 sequencing primer was added to the treated sample and the sample was sequenced by the USC/Norris Comprehensive Cancer Center DNA Sequencing Core Facility.

Digital MethyLight Evaluation Experiments. Each bisulfite-converted DNA sample was mixed with 200 µM dNTPs, 0.3 µM forward and reverse PCR primers, 0.1 µM probe, 3.5 mM MgCl$_2$, 0.01% Tween-20, 0.05% gelatin and 50 units of Taq polymerase in a 2.85 ml total volume. The PITX2 MethyLight primers were obtained from BioSearch Technologies and are as follows: forward, 5'-AGT TCG GTT GCG CGG TT-3' (SEQ ID NO:7); reverse, 5'-TAC TTC CCT CCC CTA CCT CGT T-3' (SEQ ID NO:8); probe, 5'-6FAM-CGA CGC TCG CCC GAA CGC TA-BHQ-1-3' (SEQ ID NO:9). The entire reaction mixture was aliquotted over a 96-well plate at 30 µl per PCR reaction well, and the PCR program used was 95° C. for 10 min, followed by 50 cycles of 95° C. for 15 seconds then 60° C. for 1 min. The number of methylated DNA molecules was scored as the number of quality real-time PCR fluorescence curves over the entire PCR plate.

For the M.SssI-DNA dilution series (FIG. 3B), M.SssI-DNA was diluted in serial 1:3 dilutions, and the MethyLight PCR reaction mixture was the same as above, except we used 16.67 units of Taq polymerase in a 0.96 ml total volume, which was distributed in 10 µl aliquots over 96 reaction wells. The Digital MethyLight PCR reactions were performed as above. The reactions were analyzed on an Opticon DNA Engine Continuous Fluorescence Detector (Bio-Rad) and the number of positive amplifications for each sample was scored.

The approximate number of bisulfite-converted DNA molecules in the most concentrated M.SssI-DNA sample was determined through the use of a TaqMan PCR reaction (C-LESS-C1), which recognizes a DNA strand that does not contain cytosines, and hence will be able to amplify the total amount of DNA (bisulfite-converted or unconverted) in a PCR reaction well.

The C-LESS forward sequence: 5'-TTG TAT GTA TGT GAG TGT GGG AGA GA-3' (SEQ ID NO:1); reverse: 5'-TTT CTT CCA CCC CTT CTC TTC C-3' (SEQ ID NO:2); probe: 5'-6FAM-CTC CCC CTC TAA CTC TAT-MGBNFQ-3' (SEQ ID NO:3). An unconverted DNA sample of known concentration was serially diluted and used as a standard curve, and the DNA concentration in the M.SssI-DNA sample was then determined. Since the C-LESS amplification of bisulfite-converted DNA will be delayed by one cycle compared to unconverted DNA, we multiplied this concentration by the PCR efficiency (1.83) of the C-LESS reaction as a correction factor. With this final concentration value, we determined the number of molecules present in the assayed DNA sample volume, and then extrapolated the number of DNA molecules for the remaining M.SssI-DNA dilution series. Based on these calculations, we detected approximately 25% of the available methylated PITX2 DNA molecules in the Digital MethyLight assay.

Comparison of Digital and Classic MethyLight assay sensitivities. M.SssI-DNA and WGA-DNA samples were individually treated with bisulfite as described above. A mixture of 25 pg bisulfite-converted M.SssI-DNA and 50 ng of bisulfite-converted WGA-DNA was analyzed for PITX2 methylation with the mixture analyzed in one well (Classic) and the remaining 95 wells of a PCR plate (Digital). The Classic MethyLight assay was performed by incubating the bisulfite-converted M.SssI- and WGA-DNA samples in one PCR reaction well with 200 µM dNTPs, 0.3 µM forward and reverse PCR primers, 0.1 µM probe, 3.5 mM $MgCl_2$, 0.01% Tween-20, 0.05% gelatin and 0.5 units of Taq polymerase in a 30 µl reaction volume. For the Digital MethyLight assay, the bisulfite-converted M.SssI- and WGA-DNA samples were mixed with 200 µM dNTPs, 0.3 µM forward and reverse PCR primers, 0.1 µM probe, 3.5 mM $MgCl_2$, 0.01% Tween-20, 0.05% gelatin and 50 units of Taq polymerase in a 2.85 ml total volume. This reaction mixture was aliquotted over 95 PCR reaction wells with 30 µl per well. This comparison was analyzed 20 times for each assay. The positive methylated PITX2 molecules are indicated by the black wells and the + symbol indicates a positive signal for each assay. The percentage of assays positive for PITX2 methylation is plotted for both Classic and Digital MethyLight assays.

Analysis of DNA methylation in plasma using Digital MethyLight. Plasma from breast cancer patients and controls was obtained from the University of Texas M.D. Anderson Cancer Center (Houston, Tex.). DNA was purified from 500 µl plasma using the Qiagen Blood DNA kit (Qiagen, Valencia, Calif.) and converted with bisulfite using the Zymo EZ DNA methylation kit (Zymo, Orange, Calif.) according to manufacturer's specifications. For each sample, an amount of bisulfite-converted DNA equivalent to 100 µl of plasma was mixed with MethyLight reactions specific for RUNX3 (SEQ ID NO:18; RUNX3-M1, HB-181), FOXE1 (SEW ID NO: 17; FOXE1-M1, HB-417) or CLDN5 (SEQ ID NO: 16; CLDN5-M1, HB-415). Each Digital MethyLight reaction was prepared with 200 µM dNTPs, 0.3 µM forward and reverse PCR primers, 0.1 µM probe, 3.5 mM $MgCl_2$, 0.01% Tween-20, 0.05% gelatin and 50 units of Taq polymerase in a 2.85 ml total volume. This volume was dispersed in 30 µl aliquots over an entire 96-well PCR reaction plate. For the multiplexed Digital MethyLight assay, an amount of bisulfite-converted DNA present in 100 µl of each plasma sample was prepared the same as above, except each MethyLight reaction was present at a concentration of 0.1 µM forward and reverse PCR primers and 0.1 µM probe. Each Digital MethyLight assay was performed on an Opticon Real-time PCR system, and the PCR program is 95° C. for 10 min, followed by 50 cycles of 95° C. for 15 seconds then 60° C. for 1 min. The number of methylated DNA molecules was scored as the number of quality real-time PCR fluorescence curves over the entire PCR plate. The MethyLight primers for RUNX3-M1 have been previously described (12). The primers for CLDN5 are as follows: forward, 5'-TGA GGG CGC GGG ATC-3' (SEQ ID NO: 10); reverse, 5'-CCT AAA CCA ACC CAA AAT ACG CT-3' (SEQ ID NO:11); probe, 5'-6FAM-CGA CCG CGA CTA AAA CAA CGA CGA ATA A-BHQ-1-3' (SEQ ID NO:12). The FOXE1 primers are: forward, 5'-GGG TTA GTT CGC GAC GAT TTT-3' (SEQ ID NO:13); reverse, 5'-CGA ACC TAA CGT CCC CGA-3' (SEQ ID NO:14); probe, 5'-6FAM-CGA ACG CTC GAC CCT TCT ACG AAA AAC T-BHQ-1-3' (SEQ ID NO: 15).

In particular aspects, about 10 ng bisulfite-converted DNA is used in a classic MethyLight reaction and 1 molecule in a Digital PCR reaction, to provide for an increased 2000-3000 fold ratio of primer to template DNA in the digital approach.

Microfluidic Digital MethyLight. Bisulfite-converted M.SssI-treated DNA (1 µg) in a 110 µl volume was concentrated to a final volume of 30 µl by speed-vac evaporation. This sample was then serially diluted 1:5 and 3.76 µl of each dilution was used for Microfluidic Digital MethyLight analysis. A mastermix for the PITX2 MethyLight assay was prepared in a 8.24 µl total volume consisting of 200 µM dNTPs, 0.3 µM forward and reverse PCR primers, 0.1 µM probe, 3.5 mM $MgCl_2$, 0.05% Tween-20, 0.05% gelatin, 0.5 units of Taq polymerase. The 11 µl total reaction volume for each serial dilution was loaded onto a Fluidigm BioMark Digital Array according to manufacturer's specifications. Each reaction was subdivided into 1,104 chambers, such that each chamber contained a 10 nl PCR reaction. The PCR program is the same as with the 96-well based Digital MethyLight assay for 50 cycles. PCR products were visualized by fluorescence emission and detection by a CCD camera contained within the BioMark platform. Images were taken at nearly every cycle throughout the PCR program, and screening the TaqMan fluorescence curves for each chamber via BioMark software eliminated false positives.

EXAMPLE 2

Digital Bisulfite Genomic DNA Sequencing

The human genome contains an abundance of DNA methylation information, and cancer-specific methylated DNA sequences are a powerful biomarker of disease, tumor recurrence and clinical outcome. Obtaining high-resolution DNA methylation information is possible via bisulfite genomic DNA sequencing, however, this assay is quite laborious and time inefficient with the required subcloning steps in order to isolate individual DNA molecules. According to particular aspects, Applicants have herein applied Digital PCR technology to bisulfite DNA sequencing to provide a method of quickly amplifying bisulfite-converted DNA of a specific locus for the purposes of obtaining high resolution DNA methylation sequence information.

Figure 2:
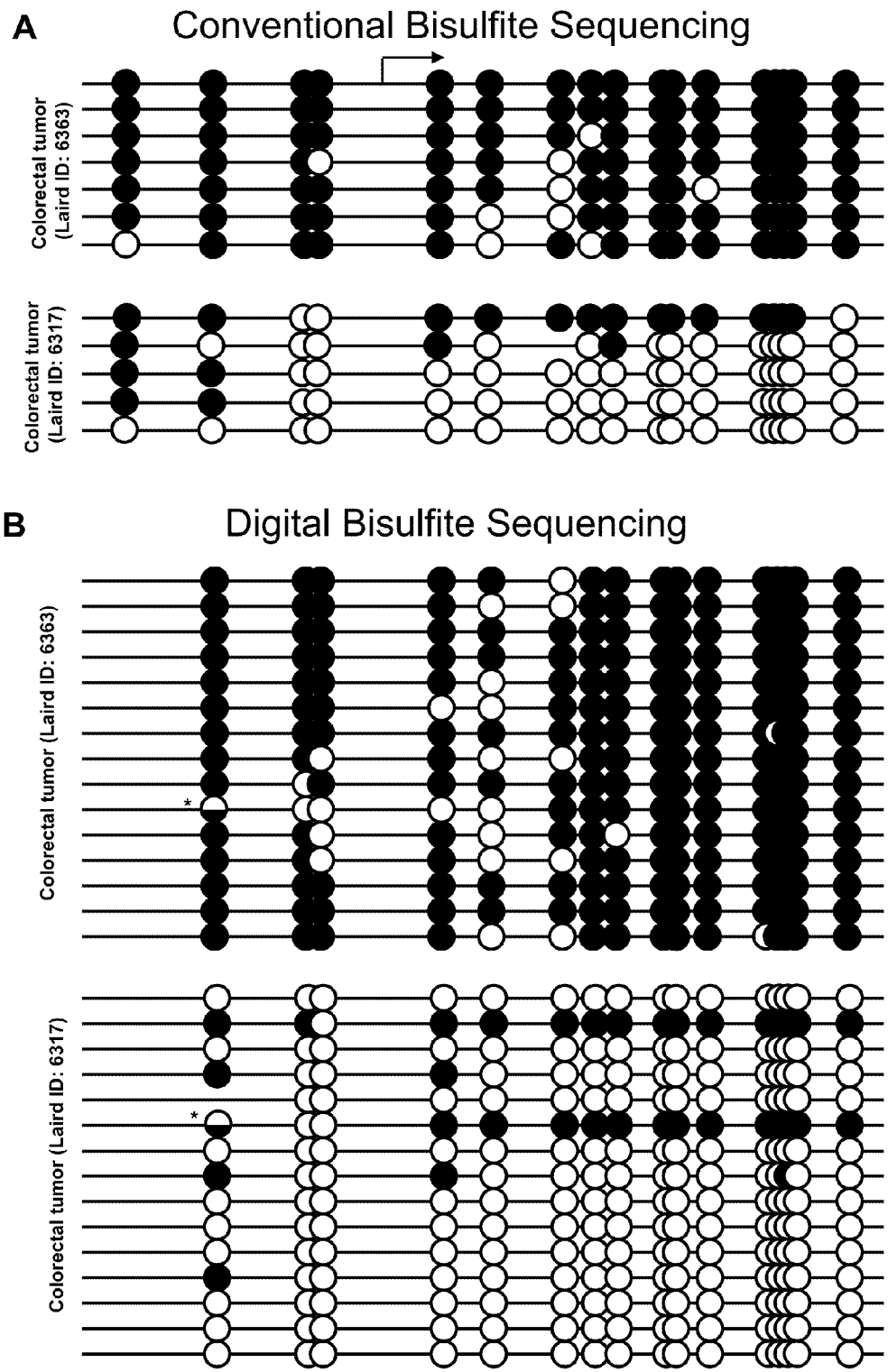
FIGS. 2A and 2B show, according to particular exemplary aspects, comparison between conventional and Digital Bisulfite Genomic DNA Sequencing of MLH1 CpG island. Bisulfite-converted tumor DNA from two colorectal cancer patients was amplified at the MLH1 locus and subject to (A) TOPO-TA cloning followed by DNA sequencing, and (B) Digital Bisulfite Genomic DNA sequencing. Each horizontal line represents an individual DNA molecule, and the circles represent CpG dinucleotides. Filled in circles are methylated CpGs while open circles are unmethylated CpGs. The asterisk (*) represents DNA sequencing reads that gave signals for both methylation and the absence of methylation for a specific CpG dinucleotide, and may be indicative of two DNA molecules amplified in the PCR reaction well.

Applicants' approach, as described in FIG. 1, was to compartmentalize and amplify individual bisulfite-converted DNA molecules in a 96-well PCR reaction plate with primers specific for bisulfite-converted DNA. PCR products derived from single DNA molecules are then identified, purified and sequenced directly without a subcloning step. To test this, we designed a PCR reaction specific for bisulfite-converted DNA sequence within the MLH1 CpG island (MLH1-C2) that can be used to compare both the conventional and digital bisulfite sequencing assays. The MLH1-C2 PCR primers are specific for bisulfite-converted DNA but are methylation-independent, such that all possible DNA methylation patterns can be amplified prior to sequencing. Tumor DNA samples from two colorectal cancer patients were used, both shown to harbor MLH1 DNA methylation by MethyLight analysis (12). Using the conventional bisulfite DNA sequencing approach first, we PCR amplified the MLH1 locus for each bisulfite-converted sample, and then ligated each PCR product into a TOPO-TA vector. These were subsequently transformed into *Escherichia Coli* and subclones composed of individual DNA molecules were isolated and sequenced. One DNA sample (6363) showed extensive methylation of the MLH1 CpG island, while individual clones of the other DNA sample (6317) showed fewer methylated CpG dinucleotides (FIG. 2A).

Applicants next performed Digital PCR on the bisulfite-converted DNA samples using the same MLH1-C2 primers. A MethyLight control reaction specific for ALU repeats was used, as well as the C-LESS TaqMan® reaction to estimate the amount of DNA to load into the PCR reaction, and each sample was diluted such that approximately 20-30 molecules were loaded over a 96-well plate to minimize the occurrence of two or more PCR templates in a single well. After PCR, wells containing valid amplified products were identified using a SYBR green melting curve analysis. An aliquot of the PCR reaction containing amplified DNA from single molecules was then purified using Exonuclease I and Shrimp Alkaline Phosphatase (Exo-SAP-IT) to remove primer and dNTPs, and was then subjected to DNA sequencing. The individual bisulfite-converted DNA molecules showed an MLH1 DNA methylation profile comparable to those derived from TOPO-TA cloning-based DNA sequencing for each sample (FIG. 2B). However, two instances were detected in which both methylated and unmethylated signals for the same CpG (highlighted by the asterisk) were observed, suggesting that this may be the result of two DNA molecules present in one PCR reaction well prior to amplification or an error in the DNA sequence analysis for this CpG dinucleotide. Regardless, Digital Bisulfite Genomic DNA sequencing represents a substantial improvement in efficiency and automation, compared to cloned bisulfite genomic sequencing.

EXAMPLE 3

The Sensitivity of Detecting Single Molecules was Compared Using Digital and Classic MethyLight Technologies DNA methylation alterations are abundant in human cancers, and one approach to early detection of cancer has been to identify tumor-derived methylated DNA in cancer patient blood. However, this strategy has been hampered by relatively low sensitivity (13). This low sensitivity stems in part from the low absolute concentration of circulating tumor-derived DNA in some patients, combined with a large excess of PCR inhibitory contaminants and competing background DNA. While digital PCR was developed as a compartmentalized PCR reaction to allow for detection and counting of discrete template molecules (9). Applicants conceived that Digital PCR technology would have an additional benefit of sequestering background DNA and contaminants into wells that do not contain amplifiable templates, thereby increasing the signal-to-noise ratio of the positive wells. Applicants tested this concept in a new application, termed Digital MethyLight, which utilizes MethyLight to interrogate a bisulfite-converted DNA sample distributed over multiple independent chambers. In the first implementation, this principle was tested in a 96-well plate format (FIG. 3A).

Figure 3:
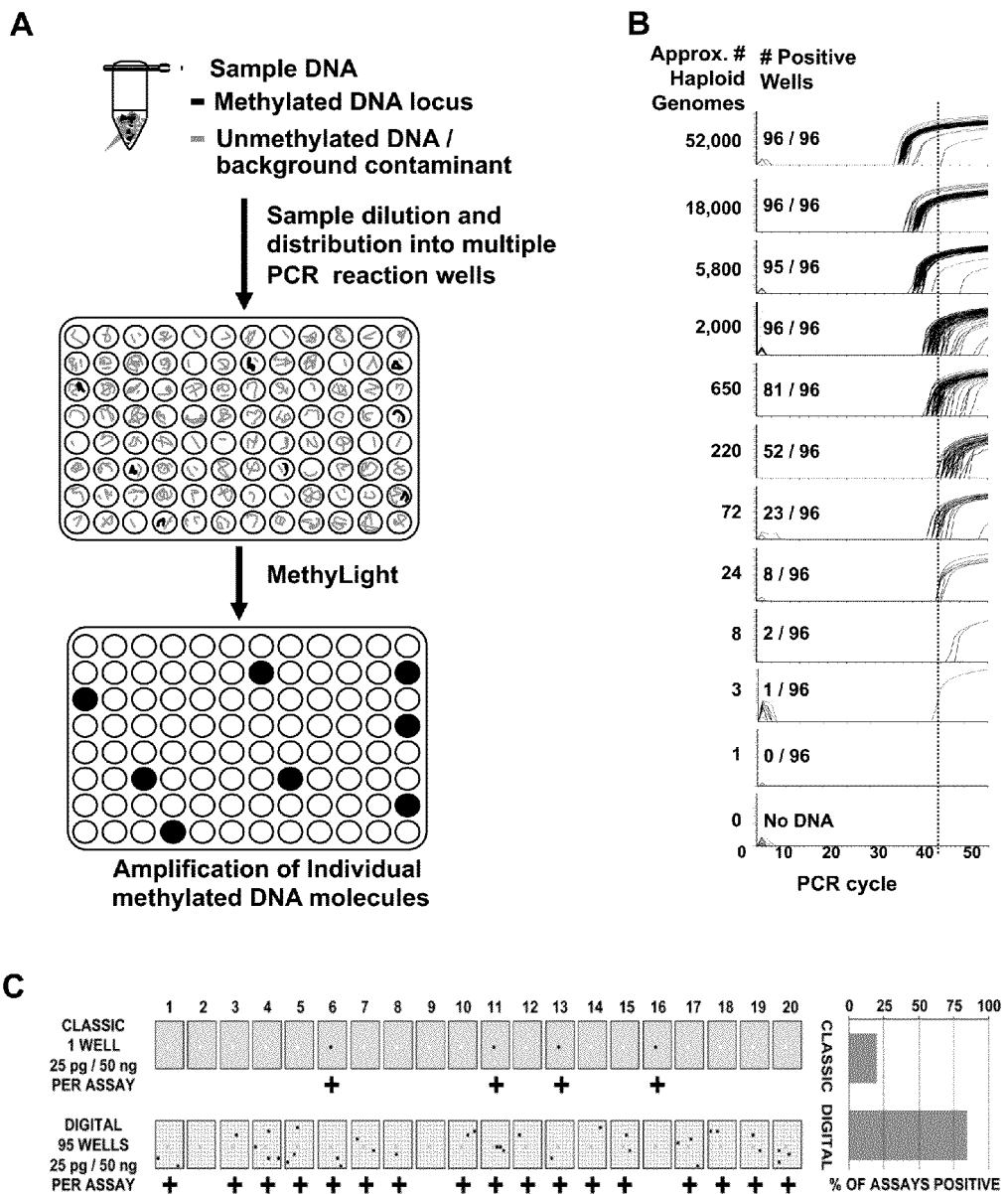
FIGS. 3A, 3B and 3C show, according to particular exemplary aspects, Digital MethyLight-based real-time PCR amplification. (A) Principle of amplifying individual methylated DNA molecules using Digital MethyLight. A bisulfite-converted DNA sample is diluted and divided into multiple PCR reaction wells such that the target methylated DNA molecules are less than one molecule per reaction well. (B) Digital MethyLight was applied to serial dilutions of in vitro methylated DNA. The PITX2 MethyLight reaction for each serial dilution was spread over 96 PCR reaction wells, the fluorescence signals for each dilution were plotted against the PCR cycle number and the number of positives were counted. The approximate number of haploid genomes was also evaluated for each dilution. The dashed vertical line represents the mean cycle threshold (Ct) value of single methylated PITX2 DNA molecules. (C) Comparison of Digital and Classic MethyLight assay sensitivities. Two identical mixtures of 25 pg M.SssI-DNA plus 50 ng of unmethylated WGA-DNA were each analyzed for PITX2 methylation with one mixture analyzed in one well (Classic) and the second analyzed over the remaining 95 wells of a PCR plate (Digital). This experiment was analyzed 20 times for each assay. The positive methylated PITX2 molecules are indicated by the black wells and the + symbol indicates a positive signal for each assay. The percentage of assays positive for PITX2 methylation is plotted for both Classic and Digital MethyLight assays.

Digital MethyLight was then applied to serial dilutions of M.SssI-treated DNA using a MethyLight reaction for methylated PITX2 (FIG. 3B). As the sample is diluted, the cycle threshold (Ct) values increase. However, as the number of available templates becomes limiting, the assay transitions from a quantitative measurement to a dichotomous measurement of stochastically distributed individual molecules. At this point, the mean C(t) value no longer increases with further dilution, as one would expect for the detection of a single, discrete molecule, as demonstrated for digital bisulfite genomic sequencing. For PITX2, this occurs at approximately cycle 40 (FIG. 3B).

A TaqMan PCR reaction (C-LESS-C1) was used, which is derived from a unique DNA sequence near the SLC24A3 gene that does not contain cytosines on one DNA strand was used to determine DNA quantities. This reaction can detect unconverted as well as bisulfite-converted DNA, and hence will be able to quantitatively measure the total amount of DNA independent of bisulfite-conversion. In comparing the number of methylated PITX2 DNA molecules to the estimate of genome equivalents in the reaction (FIG. 1B), Applicants found an approximate 25% sensitivity of detecting and amplifying individual methylated PITX2 DNA molecules using Digital MethyLight (FIG. 3B).

The sensitivity of Digital MethyLight was compared with classic MethyLight under challenging conditions of a large excess of unmethylated DNA. We mixed 25 pg of M.SssI-treated, bisulfite-converted DNA (equivalent of approximately three to four cells) with a 2,000-fold molar excess of genomic DNA devoid of DNA methylation by whole genome amplification. This mixture was analyzed 20 times for PITX2 methylation, by both Classic and Digital MethyLight assays on 96-well PCR reaction plates, with one well of each plate dedicated to the classic MethyLight assay and the remaining 95 wells of each plate assayed digitally (FIG. 3C). Only four of the 20 classic assays (20%) detected PITX2 methylation. However, 17 of 20 Digital MethyLight assays (85%) were able to detect PITX2 methylation, with many digital assays detecting multiple methylated PITX2 loci, indicating that Digital MethyLight can detect methylated DNA molecules with an increased sensitivity compared to classic MethyLight.

EXAMPLE 4

Microfluidic Digital MethyLight

Even though Digital MethyLight can detect single methylated DNA molecules, each 96-well assay is reagent intensive. Therefore, Applicants tested Digital MethyLight for its ability to detect single methylated PITX2 molecules on the Fluidigm microfluidic platform (14,15) in which 12 DNA samples can be assayed simultaneously. Each PCR reaction is compartmentalized into 1,104 individual 10 nl reaction chambers, enabling the detection of single methylated DNA molecules in an 11 µl total reaction volume. Individually amplified methylated DNA molecules were then visualized via the MethyLight probe fluorescence signals using a high-resolution CCD camera. Microfluidic MethyLight technology was applied to serial dilutions of M.SssI-treated DNA (FIG. 4). Using the microfluidic platform, Applicants were also able to amplify single methylated PITX2 molecules. This high-throughput Digital MethyLight approach can, therefore, successfully and sensitively detect single molecule DNA methylation events in small PCR reaction volumes.

EXAMPLE 5

Digital MethyLight was Tested for its Ability to Detect Single Methylated PITX2 Molecules in Sera of Pancreatic Cancer Patients Digital MethyLight was next tested for its ability to detect single methylated PITX2 molecules in sera of pancreatic cancer patients. PITX2 was selected after a rigorous pre-screen of 119 gene loci in nine pancreatic tumors and a counter-screen against serum DNA from apparently healthy controls (data not shown). Digital MethyLight technology was applied to a Fluidigm microfluidic platform. Each microfluidic PCR reaction is compartmentalized into 1200 individual 5 nl reaction chambers, enabling the detection of single methylated DNA molecules at a small (6 µl) total reaction volume. Individually amplified methylated DNA molecules are visualized via the fluorescence signal from the MethyLight PCR product. The application of microfluidic MethyLight technology to serial dilutions of M.SssI-treated DNA (FIG. 4) and serum DNA samples of pancreatic cancer patients also amplified single methylated PITX2 molecules.

EXAMPLE 6

Detection of Methylated DNA in Breast Cancer Patient Plasma Using Digital MethyLight The Digital MethyLight technology was also tested on biological samples for the detection of tumor-derived, methylated DNA in the bloodstream. Digital MethyLight was applied to DNA isolated from plasma of 44 breast cancer patients of different stages of disease and 13 apparently normal individuals. MethyLight reactions specific for methylated CpG islands located in the promoter regions of FOXE1, CLDN5 and RUNX3 were selected for this analysis. Using classic MethyLight, these reactions showed high cancer specificity in breast cancer tumor samples, and did not detect methylation in a test panel of plasma and white blood cells (WBC) from age-matched healthy control individuals (data not shown). As a result, these reactions would generate a low background signal from lysed WBCs and other free DNAs present in the breast cancer patient plasma samples.

Figure 5:
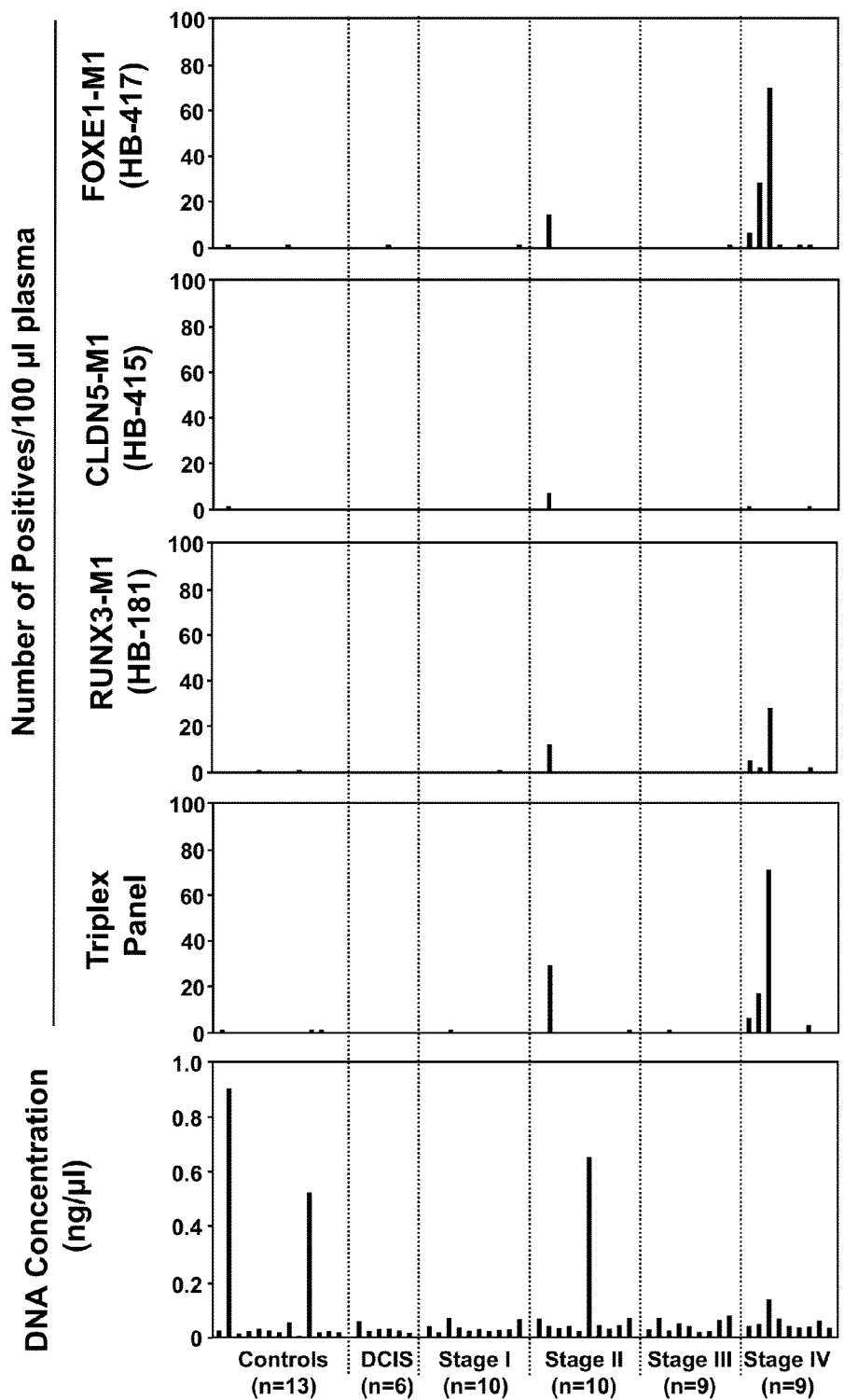
FIG. 5 shows, according to particular exemplary aspects, Digital MethyLight on plasma samples from 44 breast cancer patients and 13 apparently healthy controls. DNA from 500 μl plasma was purified, busulfite converted and a DNA amount from 100 μl plasma was subject to Digital MethyLight. Each sample was analyzed individually for FOXE1, CLDN5 or RUNX3 methylation, as well as with all three reactions multiplexed. The results are presented as the number of methylated molecules per 100 μl plasma for each sample. The DNA concentration in each plasma sample was estimated based on a TaqMan® reaction specific for ALU repetitive elements.

Each of the three MethyLight reactions was tested separately on bisulfite-converted DNA isolated from 100 µl plasma using Digital MethyLight, and methylated DNA molecules were detected in one stage II and several stage IV breast cancer patients, with the most abundant methylation seen in Stage IV patients (FIG. 5). Methylated FOXE1 and RUNX3 molecules were more abundant than methylated CLDN5 DNA, especially in the stage IV cases. To increase the sensitivity of methylated DNA detection, we multiplexed all three MethyLight reactions into one assay for each plasma sample. As expected, we detected an approximately cumulative number of DNA hypermethylation events using the multiplexed assay, thereby increasing sensitivity. One of the stage IV cases with background methylation levels of the individual markers became more evident after multiplexing, rising slightly above background levels (FIG. 5). Applicants found that although there were plasma samples with substantial amounts of free DNA, this did not correlate with the number of methylated DNA molecules in patient or control plasma based on an assessment of DNA quantities using a TaqMan PCR reaction specific for ALU repeats (FIG. 5). Applicants conclude that the careful selection of MethyLight reactions effectively avoided detecting DNA methylation from lysed white blood cells or background DNA methylation in plasma.

References cited for Examples 1-6; all of which are incorporated by reference herein:

1. Jones, P. A. and Baylin, S. B. (2007) The epigenomics of cancer. *Cell*, 128, 683-692.
2. Laird, P. W. (2005) Cancer epigenetics. *Hum Mol Genet*, 14 Spec No 1, R65-76.
3. Cottrell, S. E. and Laird, P. W. (2003) Sensitive detection of DNA methylation. *Ann N Y Acad Sci*, 983, 120-130.
4. Hsieh, C. L. and Jones, P. A. (2003) Meddling with methylation. *Nat Cell Biol*, 5, 502-504.
5. Laird, P. W. (2003) The power and the promise of DNA methylation markers. *Nat Rev Cancer*, 3, 253-266.
6. Herman, J. G., Graff, J. R., Myohanen, S., Nelkin, B. D. and Baylin, S. B. (1996) Methylation-specific PCR: a novel PCR assay for methylation status of CpG islands. *Proc Natl Acad Sci USA*, 93, 9821-9826.
7. Eads, C. A., Danenberg, K. D., Kawakami, K., Saltz, L. B., Blake, C., Shibata, D., Danenberg, P. V. and Laird, P. W. (2000) MethyLight: a high-throughput assay to measure DNA methylation. *Nucleic Acids Res.*, 28, e32.
8. Fatemi, M., Pao, M. M., Jeong, S., Gal-Yam, E. N., Egger, G., Weisenberger, D. J. and Jones, P. A. (2005) Footprinting of mammalian promoters: use of a CpG DNA methyltransferase revealing nucleosome positions at a single molecule level. *Nucleic Acids Res*, 27, e176.
9. Vogelstein, B. and Kinzler, K. W. (1999) Digital PCR. *Proc Natl Acad Sci USA*, 96, 9236-9241.
10. Weisenberger, D. J., Campan, M., Long, T. I., Kim, M., Woods, C., Fiala, M. E., Ehrlich, M. and Laird, P. W. (2005) Analysis of repetitive element methylation by MethyLight analysis. submitted.
11. Weisenberger, D. J., Campan, M., Long, T. I., Kim, M., Woods, C., Fiala, E., Ehrlich, M. and Laird, P. W. (2005) Analysis of repetitive element DNA methylation by MethyLight. *Nucleic Acids Res*, 33, 6823-6836.
12. Weisenberger, D. J., Siegmund, K. D., Campan, M., Young, J., Long, T. I., Faasse, M. A., Kang, G. H., Widschwendter, M., Weener, D., Buchanan, D. et al. (2006) CpG island methylator phenotype underlies sporadic microsatellite instability and is tightly associated with BRAF mutation in colorectal cancer. *Nat Genet*, 38, 787-793.
13. Laird, P. W. (2003) The power and the promise of DNA methylation markers. Nature Rev. *Cancer*, 3, 253-266.
14. Ottesen, E. A., Hong, J. W., Quake, S. R. and Leadbetter, J. R. (2006) Microfluidic digital PCR enables multigene analysis of individual environmental bacteria. *Science*, 314, 1464-1467.
15. Thorsen, T., Maerkl, S. J. and Quake, S. R. (2002) Microfluidic large-scale integration. *Science*, 298, 580-584.
16. Lau, Q. C., Raja, E., Salto-Tellez, M., Liu, Q., Ito, K., Inoue, M., Putti, T. C., Loh, M., Ko, T. K., Huang, C. et al. (2006) RUNX3 is frequently inactivated by dual mechanisms of protein mislocalization and promoter hypermethylation in breast cancer. *Cancer Res*, 66, 6512-6520.
17. Lofton-Day, C., Model, F., DeVos, T., Liebenberg, V., Day, R. W. and Sledziewski, A. (2007) Clinical case-control study in plasma shows that the DNA methylation biomarker, Septin 9, detects 70% of Stage I-III colorectal cancer patients. *Proceedings of the American Association of Cancer Research*, 100*th Annual Meeting*, Los Angeles, Calif.
18. Taylor, K. H., Kramer, R. S., Davis, J. W., Guo, J., Duff, D. J., Xu, D., Caldwell, C. W. and Shi, H. (2007) Ultradeep bisulfite sequencing analysis of DNA methylation patterns in multiple gene promoters by 454 sequencing. *Cancer Res*, 67, 8511-8518.

TABLE 1

Exemplary primers, probes, genomic sequences and CpG island sequences.

| HGNC ID | Reaction ID | Forward Primer Sequence | Reverse Primer Sequence | Methyl Light Probe Sequence |
|---|---|---|---|---|
| CLDN5 | CLDN5-M1 | TGAGGGCGCGGGATC | CCTAAACCAACCCAAATACGCT | 6FAM-CGACCGCGGACTAAAACAACGAC-GAATAA-BHQ-1 |
| FOXE1 | FOXE1-M1 | GGGTTAGTTCGCGACGATTTT | CGAACCTAACGTCCCCGA | 6FAM-CGAACGCTCGACCCTTCTAC-GAAAAACT-BHQ-1 |
| PITX2 | PITX2-M2 | AGTTCGGTTGCGCGGTT | TACTTCCCTCCCCTACCTCGTT | 6FAM-CGACGCTCGCCCGAACGCTA-BHQ-1 |
| RUNX3 | RUNX3-M1 | CGTTCGATGGTGGACGTGT | GACGAACAACGTCTTATTACAACGC | 6FAM-CGCACGAACTCGCCTACGTAATCCG-BHQ-1 |
| MLH1 | MLH1-C1 | GATTGGTATTTAAGTTGTTTAATTAATAG | CAATCATCTCTTTAATAACATTAACTAA | |

| HGNC ID | Reaction ID | PCR Start Genomic Coordinate (UCSC, May 2006) | PCR End Genomic Coordinate (UCSC, May 2006) | GenBank Accession | PCR Start Genomic Coordinate (GenBank) | PCR End Genomic Coordinate (GenBank) | CpG Island Start Coordinate (GenBank) | CpG Island End Coordinate (GenBank) |
|---|---|---|---|---|---|---|---|---|
| CLDN5 | CLDN5-M1 | chr2: 17892102 | chr2: 17892195 | AC000088 | 28843 | 28936 | 27284 | 29273 |
| FOXE1 | FOXE1-M1 | chr9: 99655888 | chr9: 99655959 | AL499604 | 72069 | 72140 | 70878 | 73824 |
| PITX2 | PITX2-M2 | chr4: 111777748 | chr4: 111777850 | AC017068 | 117302 | 117404 | 116561 | 118309 |
| RUNX3 | RUNX3-M1 | chr1: 25128674 | chr1: 25128790 | AL023096 | 64646 | 64762 | 63661 | 67973 |
| MLH1 | MLH1-C1 | ch3: 37009881 | chr3: 37010150 | AC011816 | 143044 | 143315 | 142038 | 143623 |

The invention claimed is:

1. A method for analyzing a small number of methylated DNA molecules in a large background of unmethylated DNA, comprising:
   obtaining a sample having genomic DNA comprising a small number of methylated genomic DNA molecules in a large background of unmethylated genomic DNA;
   contacting the genomic DNA molecules with a reagent or series of reagents suitable to distinguish between methylated and nonmethylated CpG dinucleotides to provide for treated genomic DNA molecules;
   compartmentalizing the treated DNA molecules over multiple PCR compartments or wells by stochastically distributing individual treated DNA molecules such that, on average, there is less than one treated DNA molecule per reaction compartment or well, and wherein at least one well or compartment has no more than a single treated DNA molecule;
   amplifying, in a first amplification reaction, portions or fragments of said compartmentalized single treated DNA molecule by means of a polymerase chain reaction (PCR) and one or more sets of primer oligonucleotides to provide for at least one amplificate of the compartmentalized single, treated DNA molecule; and
   detecting, in real-time during the first amplification, of the at least one amplificate, wherein the methylation state of at least one CpG dinucleotide sequence thereof is determined, and wherein analyzing a small number of methylated genomic DNA molecules in a large background of unmethylated genomic DNA is provided for.

2. The method of claim 1, wherein the reagent or series of reagents comprises at least one reagent selected from the group consisting of bisulfite, hydrogen sulfite and disulfite.

3. The method of claim 1, comprising multiplexing with a plurality of primer sets to provide for amplification of a respective plurality of different DNA amplificate fragments.

4. The method of claim 3, wherein at least three, at least five, or at least ten different fragments, each having a length of about 100 to about 2000 base pairs, are amplified.

5. The method of claim 1, wherein the sample comprising genomic DNA is a plasma or serum sample.

6. The method of claim 5, further comprising determining the number of methylated molecules of a particular locus relative to a specific volume of plasma or serum.

7. The method of claim 5, wherein the plasma sample is at least one selected from the group consisting of a breast cancer patient, pancreatic patient, and a colorectal cancer patient.

8. The method of claim 7, wherein the breast cancer patient is a Stage II or Stage IV breast cancer patient.

9. The method of claim 1, wherein the ratio of primer to methylated template DNA is kept high.

10. The method of claim 1, wherein the PCR reactions are compartmentalized into a plurality of individual microfluidic reaction chambers to provide for microfluidic analysis.

11. The method of claim 1, wherein, prior to compartmentalizing, determining the Ct value to determine the amount of treated DNA to load into each PCR compartments or well.

12. The method of claim 11, wherein the Ct values are calibrated, using a suitable control reaction, to the C-LESS signal using genomic DNA as a standard.

13. The method of claim 1, wherein about 20 to about 30 DNA molecules are stochastically distributed and compartmentalized over the multiple PCR compartments or wells.

14. The method of claim 1, comprising determining the methylation status of one or more CpG dinucleotides within at least one of FOXE1 (SEQ ID NO:17), CLDN5 (SEQ ID NO:16), and RUNX3 (SEQ ID NO:18).

15. The method of claim 1, comprising:
   obtaining a sample having genomic DNA comprising a small number of methylated genomic DNA molecules in a large background of unmethylated genomic DNA;
   contacting the genomic DNA molecules with a reagent or series of reagents suitable to distinguish between methylated and nonmethylated CpG dinucleotides to provide for treated genomic DNA molecules;
   compartmentalizing the treated DNA molecules over multiple PCR compartments or wells by stochastically distributing individual treated DNA molecules such that, on average, there is less than one treated DNA molecule per reaction compartment or well, and wherein at least one well or compartment has no more than a single treated DNA molecule;
   amplifying, in a first amplification reaction, portions or fragments of said compartmentalized single treated DNA molecule by means of a polymerase chain reaction (PCR) and one or more sets of primer oligonucleotides to provide for at least one amplificate of the compartmentalized single, treated DNA molecule; and
   sequencing the at least one amplificate, wherein at least one individual genomic DNA molecule CpG methylation pattern of a methylated genomic DNA molecule in a large background of unmethylated genomic DNA is determined.

16. The method of claim 15, wherein about 20 to about 30 individual molecules are assayed and sequenced to determine methylation patterns at a candidate gene locus.

17. The method of claim 15, further comprising the use of melting curve analysis to identify the melting curve of the PCR product in at least one of the compartments or wells.

* * * * *